(12) United States Patent
Huang et al.

(10) Patent No.: US 12,427,253 B2
(45) Date of Patent: Sep. 30, 2025

(54) INSERTION DEVICE FOR A BIOSENSOR AND INSERTION METHOD THEREOF

(71) Applicant: BIONIME CORPORATION, Taichung (TW)

(72) Inventors: Chun-Mu Huang, Taichung (TW); Chieh-Hsing Chen, Taichung (TW); Chen-Hao Lee, Taichung (TW); Kuan-Lin Chang, Taichung (TW)

(73) Assignee: BIONIME CORPORATION, Taichung (TW)

( * ) Notice: Subject to any disclaimer, the term of this patent is extended or adjusted under 35 U.S.C. 154(b) by 148 days.

(21) Appl. No.: 16/983,101

(22) Filed: Aug. 3, 2020

(65) Prior Publication Data

US 2021/0030961 A1 Feb. 4, 2021

Related U.S. Application Data

(60) Provisional application No. 62/882,140, filed on Aug. 2, 2019.

(30) Foreign Application Priority Data

Jan. 10, 2020 (TW) .................................. 109100958

(51) Int. Cl.
*A61M 5/20* (2006.01)
*A61B 5/00* (2006.01)
(Continued)

(52) U.S. Cl.
CPC ....... *A61M 5/2033* (2013.01); *A61B 5/14503* (2013.01); *A61B 5/14532* (2013.01);
(Continued)

(58) Field of Classification Search
CPC ............ A61B 5/14503; A61B 5/14532; A61B 5/6849; A61B 5/6833; A61B 2560/0443;
(Continued)

(56) References Cited

U.S. PATENT DOCUMENTS

| | | | |
|---|---|---|---|
| 6,093,172 | A | 7/2000 | Funderburk et al. |
| 7,381,184 | B2 | 6/2008 | Funderburk et al. |

(Continued)

FOREIGN PATENT DOCUMENTS

| | | |
|---|---|---|
| CN | 109893131 A | 6/2019 |
| CN | 109924952 A | 6/2019 |

(Continued)

OTHER PUBLICATIONS

Search Report issued to European counterpart application No. 20189213.0 by the EPO on Nov. 27, 2020.

*Primary Examiner* — Matthew Kremer
*Assistant Examiner* — Meghan R Kumar
(74) *Attorney, Agent, or Firm* — Bayramoglu Law Offices LLC

(57) ABSTRACT

An insertion device includes a cover body and an insertion module. The insertion module is disposed in the cover body, and includes a main body, an insertion seat, a pre-compressed first elastic member, a retraction seat and a pre-compressed second elastic member. The restoring force of the pre-compressed first elastic member is configured not to act on the cover body during depression of the cover body.

17 Claims, 33 Drawing Sheets

(51) Int. Cl.
*A61B 5/145* (2006.01)
*A61M 5/32* (2006.01)

(52) U.S. Cl.
CPC ......... *A61B 5/6849* (2013.01); *A61M 5/3234* (2013.01); *A61B 5/6833* (2013.01); *A61B 2560/0443* (2013.01); *A61B 2560/063* (2013.01); *A61M 2005/206* (2013.01); *A61M 2205/3303* (2013.01)

(58) Field of Classification Search
CPC .......... A61B 2560/063; A61M 5/2033; A61M 5/3234; A61M 2005/206; A61M 2205/3303
See application file for complete search history.

(56) References Cited

U.S. PATENT DOCUMENTS

| | | | |
|---|---|---|---|
| 7,699,807 B2 * | 4/2010 | Faust | ................ A61B 5/14503 604/157 |
| 8,280,475 B2 | 10/2012 | Brister et al. | |
| 8,439,838 B2 | 5/2013 | Mogensen et al. | |
| 8,696,570 B2 | 4/2014 | Yodfat et al. | |
| 8,870,822 B2 | 10/2014 | Thalmann et al. | |
| 9,186,098 B2 | 11/2015 | Lee et al. | |
| 10,278,732 B2 | 5/2019 | Schoonmaker et al. | |
| 10,413,183 B2 | 9/2019 | Antonio et al. | |
| 2004/0133164 A1 | 7/2004 | Funderburk et al. | |
| 2010/0217105 A1 * | 8/2010 | Yodfat | ............... A61B 5/14532 606/108 |
| 2017/0188912 A1 | 7/2017 | Halac et al. | |
| 2018/0368772 A1 | 12/2018 | Gray et al. | |
| 2019/0072912 A1 | 3/2019 | Pandya et al. | |
| 2019/0223768 A1 | 7/2019 | Muller et al. | |
| 2019/0365297 A1 | 12/2019 | Stafford | |
| 2020/0178899 A1 * | 6/2020 | Chae | ................ A61B 5/150244 |

FOREIGN PATENT DOCUMENTS

| | | | |
|---|---|---|---|
| CN | 109998560 A | 7/2019 | |
| EP | 3251596 A1 | 12/2017 | |
| TW | M576726 U | 4/2019 | |
| WO | 2011119896 A1 | 9/2011 | |
| WO | 2017116915 A1 | 7/2017 | |
| WO | WO-2018136898 A1 * | 7/2018 | ......... A61B 17/3468 |
| WO | 2018222012 A1 | 12/2018 | |

* cited by examiner

INSERTION DEVICE FOR A BIOSENSOR AND INSERTION METHOD THEREOF

CROSS-REFERENCE TO RELATED APPLICATION

This application claims priority of U.S. Provisional Patent Application No. 62/882,140, filed on Aug. 2, 2019, and Taiwanese Patent Application No. 109100958, filed on Jan. 10, 2020.

FIELD

The disclosure relates to an insertion device and an insertion method thereof, and more particularly to an insertion device for a biosensor and an insertion method thereof.

BACKGROUND

A conventional insertion device disclosed in U.S. Pat. No. 10,413,183 is for inserting a biosensor into a host, and includes a plunger, and a piercing member to which the sensor assembly is mounted.

The piercing member is inserted into the host upon depression of the plunger, but is not separated from the host until the plunger is released. Accordingly, the conventional insertion device is operated via a two-action operation. When an operator fails to promptly release the plunger, the piercing member remains to be inserted into the host and may cause discomfort of the host.

SUMMARY

Therefore, an object of the disclosure is to provide an insertion device that can alleviate the drawback of the prior art.

According to the disclosure, the insertion device includes a cover body, an insertion module. The cover body has an accommodating space. The insertion module is disposed in the accommodating space, and includes a main body, a main cover, an insertion seat, a pre-compressed first elastic member, a retraction seat, a pre-compressed second elastic member, a base and a sensor assembly. The main body is coupled to the main cover, and cooperates with the main cover to define a displacement space therebetween. The insertion seat is removably positioned in the main cover, and is able to move in the displacement space between the main body and the main cover. The pre-compressed first elastic member has two opposite ends that respectively abut against the insertion seat and the main cover. The retraction seat is removably positioned relative to the insertion seat. The pre-compressed second elastic member has two opposite ends that respectively abut against the insertion seat and the retraction seat. The base is separably positioned relative to the main body. The sensor assembly is to be separably mounted to the base. When the cover body is depressed, the insertion seat is driven by a restoring force of the pre-compressed first elastic member to perform an automatic-insertion operation and to collapse a limiting structure between the insertion seat and the main cover. After the automatic-insertion operation is done, the cover body is positioned relative to the main body without rebounding, and a limiting structure between the insertion seat and the retraction seat collapses upon the collapse of the limiting structure between the insertion seat and the main cover, so that the retraction seat is driven by a restoring force of the pre-compressed second elastic member to perform an automatic-retraction operation. The restoring force of the pre-compressed first elastic member is configured not to act on the cover body during depression of the cover body.

Another object of the disclosure is to provide an insertion method that can alleviate the drawback of the prior art.

According to the disclosure, the insertion method includes: an insertion device including a displacement space that is cooperatively defined by a main cover and a main body; an insertion module disposed in the displacement space, the insertion module being movable in the displacement space by compressed first and second elastic members therein so as to perform an automatic-insertion operation and an automatic-retraction operation; an insertion limiting structure disposed between the insertion module and the main body for removably positioning the insertion module at a pre-insertion position; and a retraction limiting structure disposed between the insertion module and the main cover, the insertion module being able to move from a post-insertion position to the pre-insertion position when the retraction limiting structure is collapsed. When the insertion device is kept being depressed, the insertion limiting structure is collapsed, and the insertion module is biased by a restoring force of the first elastic member to move downwardly to perform the automatic-insertion operation. The retraction limiting structure is collapsed immediately after the insertion module finishing the automatic-insertion operation, such that the insertion module is biased by a restoring force of the second elastic member to move upwardly to perform the automatic-retraction operation. The insertion module positions a sensor assembly thereof onto abase during the automatic-insertion operation. A time needed for performing the automatic-insertion operation and the automatic-retraction operation is no more than 100 milliseconds, no more than 8 milliseconds, no more than 4 milliseconds or no more than 2 milliseconds.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
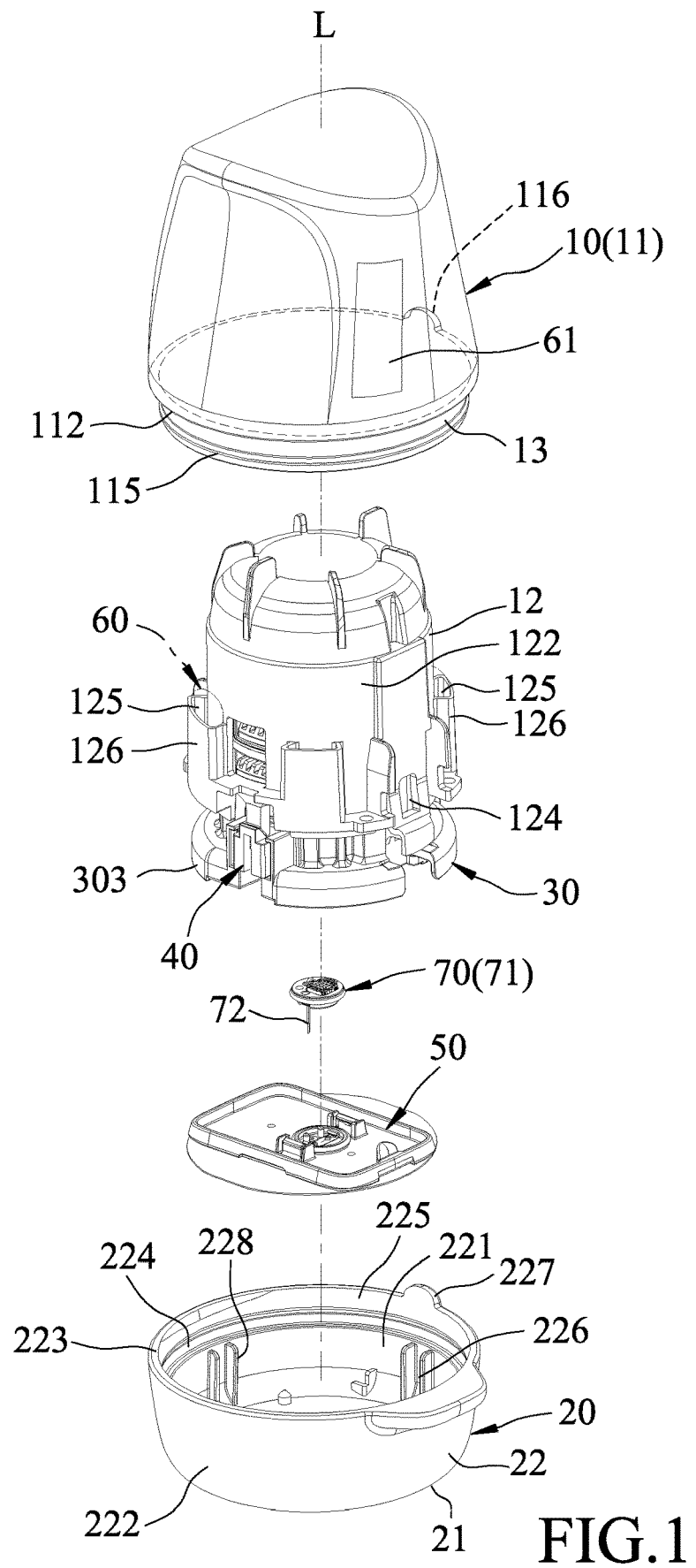
FIG. 1 is an exploded perspective view illustrating a first embodiment of the insertion device according to the disclosure.
Figure 2:
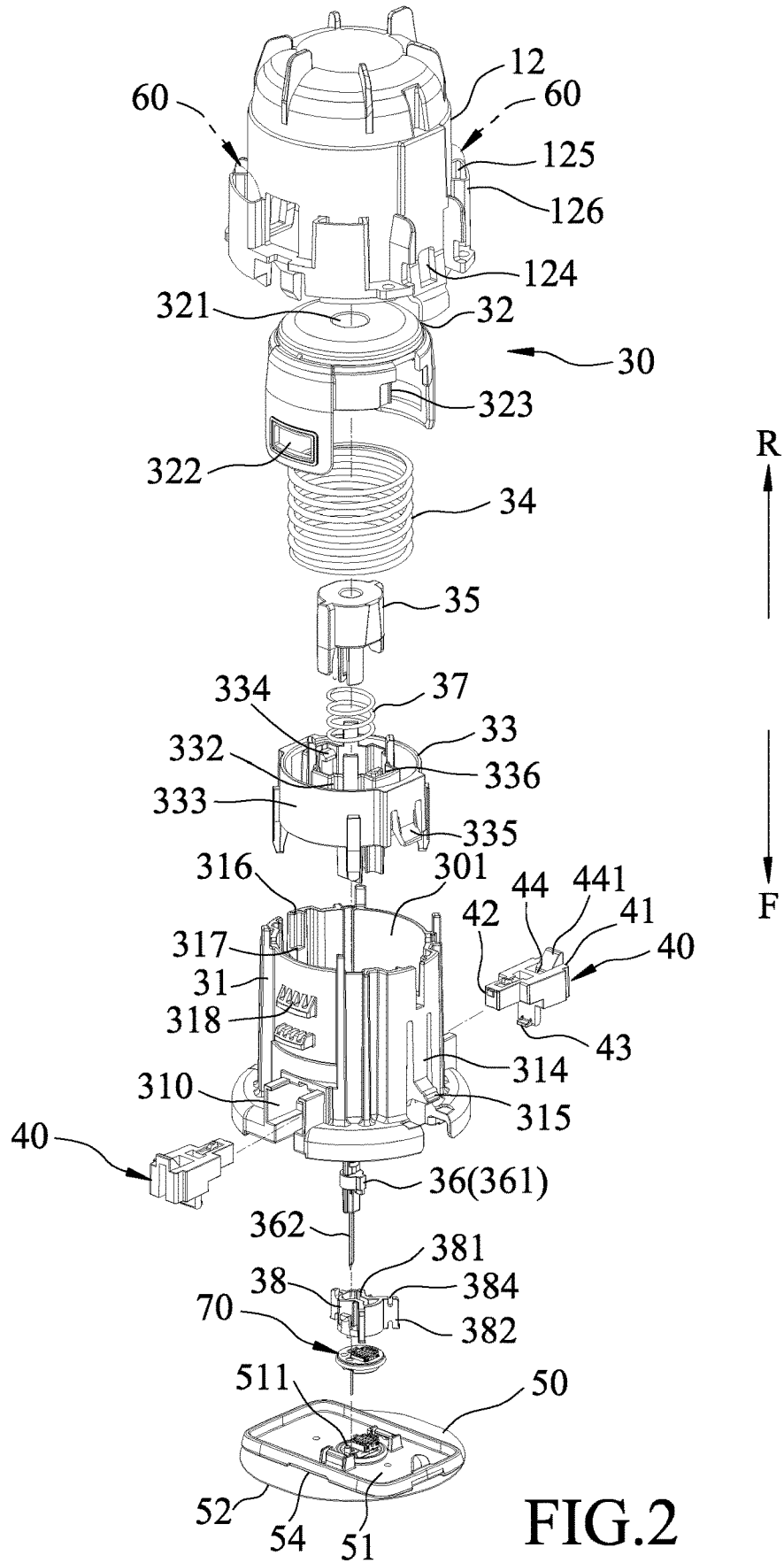
FIG. 2 is another exploded perspective view illustrating the first embodiment.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 4, a first embodiment of the insertion device according to the disclosure is for inserting a sensor into a host. The insertion device may be in the form of a canister (e.g., a desiccant canister), but is not limited to such. The insertion device includes an upper casing 10 and an insertion module 30.

Figure 4:
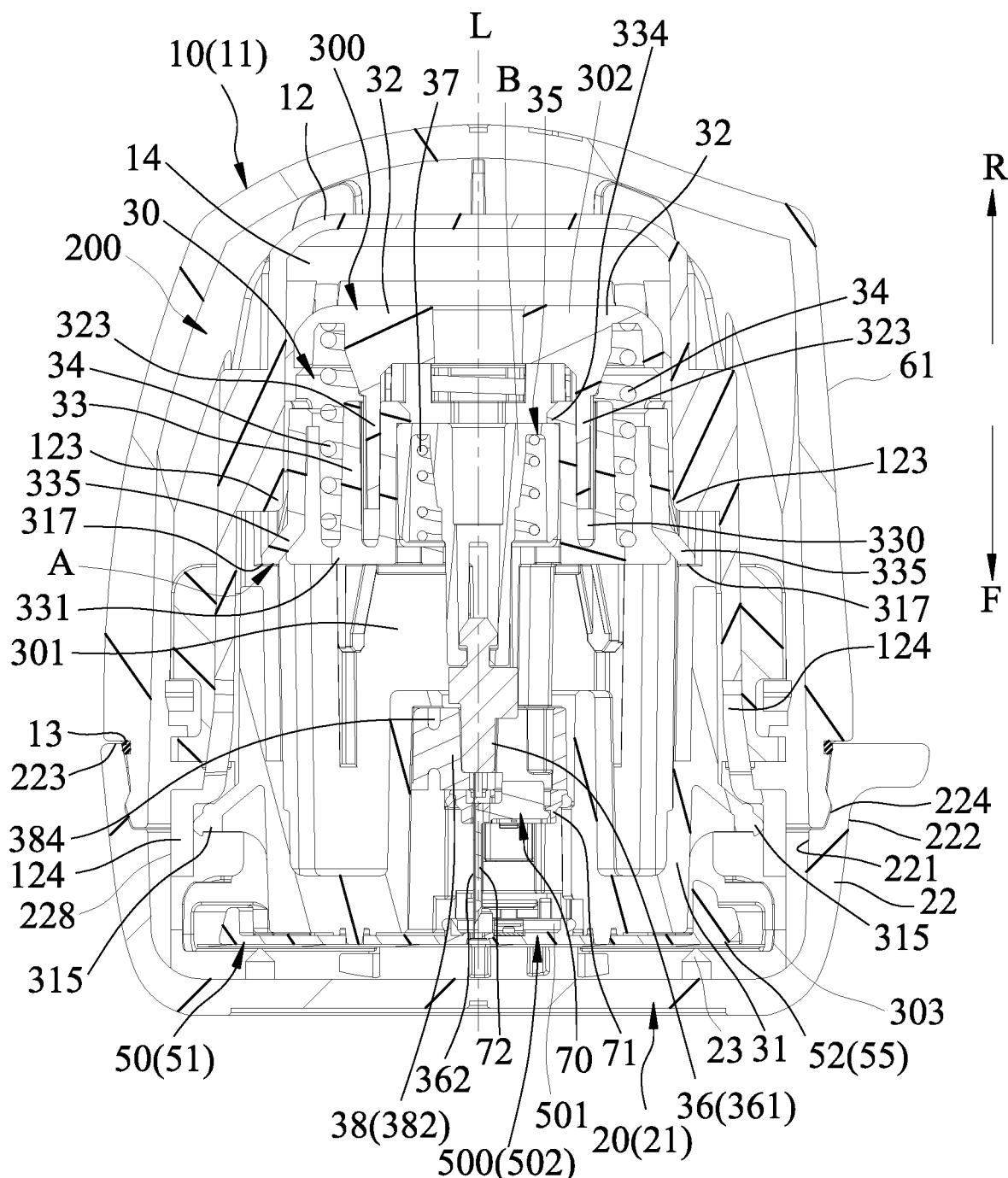
FIG. 4 is a sectional view taken along line IV-IV in FIG. 3.

The upper casing 10 has an accommodating space 14 (see FIG. 4), and a pair of casing engaging structures 124 (see FIG. 4).

The insertion module 30 is disposed in the accommodating space 14, and includes a main body assembly 300, an insertion seat 33, a first elastic member 34, a retraction seat 35, a second elastic member 37, a base 50 and a sensor assembly 70.

Figure 3:
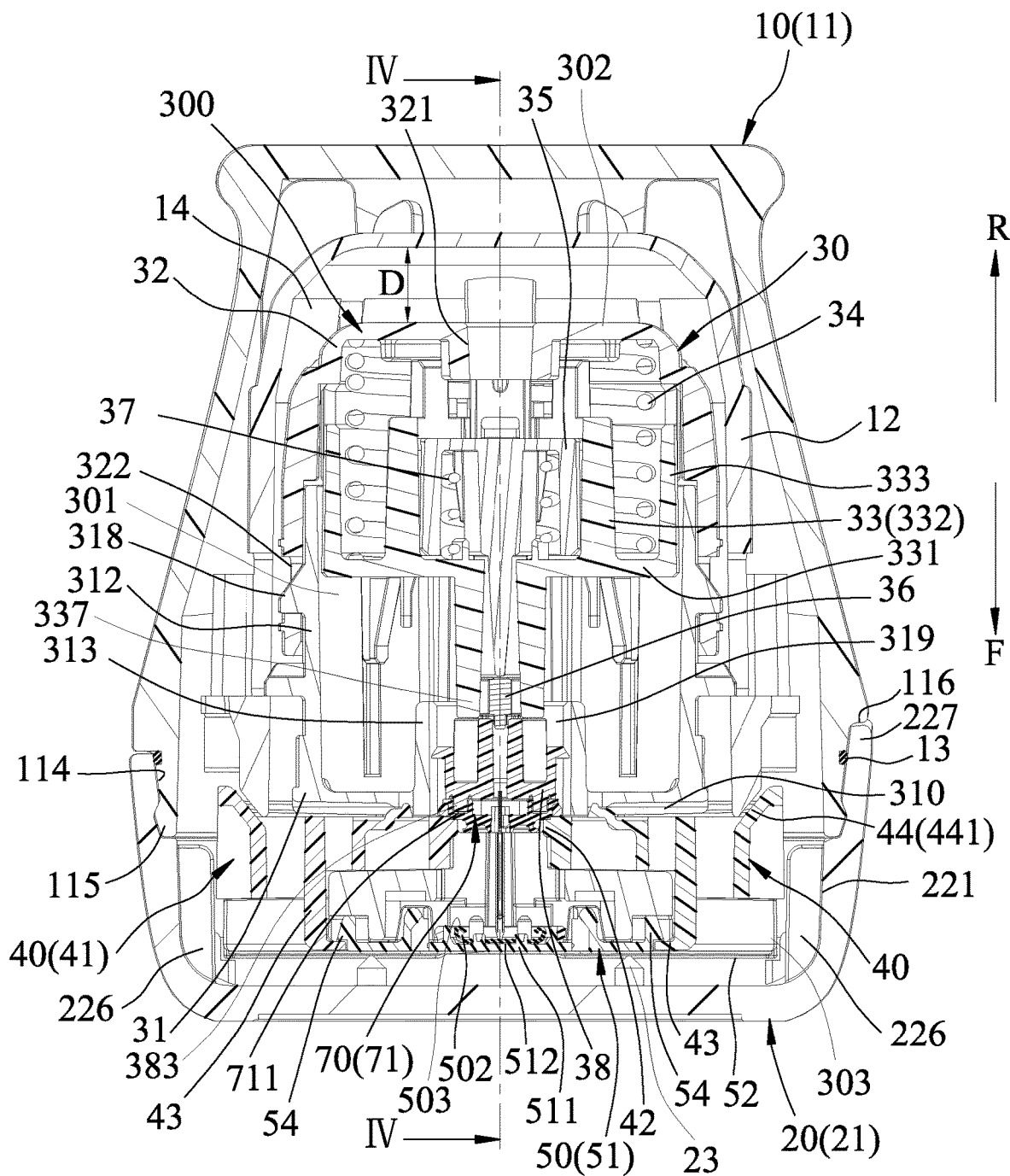
FIG. 3 is a sectional view illustrating of first embodiment, illustrating a sensor of a container in a state to be implanted.

With particular reference to FIGS. 3 and 4, the main body assembly 300 includes an upper portion 302, and a lower portion 303 that cooperates with the upper portion 302 to define a displacement space 301 therebetween. The lower portion 303 of the main body assembly 300 has a pair of body engaging structures 315 that abut against inner sides of the casing engaging structures 124 of the upper casing 10, and that are able to respectively engage the casing engaging structures 124 of the upper casing 10 when the upper casing 10 is depressed downwardly.

The insertion seat 33 is removably positioned in the upper portion 302 of the main body assembly 300, and is able to move in the displacement space 301 between the upper portion 302 and the lower portion 303 along an axial line (L).

The upper casing 10 has a pair of urging portions 123 (see FIG. 4). The lower portion 303 of the main body assembly 300 has a pair of stopping portions 317 (see FIG. 4). The insertion seat 33 has a pair of buckle portions 335 (see FIG. 4) that respectively and separably abut against the stopping portions 317 of the lower portion 303 of the main body assembly 300 so as to position the insertion seat 33 relative to the main body assembly 300, and that are able to be respectively pushed by the urging portions 123 of the upper casing 10 to be respectively separated from the stopping portions 317 of the lower portion 303 of the main body assembly 300. The buckle portions 335 of the insertion seat 33 respectively and separably abut the stopping portions 317 of the lower portion 303 of the main body assembly 300 so as to form an insertion limiting structure (A) (see FIG. 4).

The insertion seat 33 further has at least one limiting groove 330 (see FIG. 4). The upper portion 302 of the main body assembly 300 has at least one limiting member 323 (see FIG. 4) that removably engages with the limiting groove 330 of the insertion seat 33. The insertion seat 33 further has at least one retraction positioning portion 334 that separably abuts against the limiting member 323 of the upper portion 302 of the main body assembly 300.

The first elastic member 34 has two opposite ends respectively abutting against the insertion seat 33 and the upper portion 302 of the main body assembly 300. In this embodiment, the first elastic member 34 may be configured as a pre-compressed spring.

The retraction seat 35 is mounted with an insertion needle 36, and is removably positioned relative to the insertion seat 33. Specifically, the retraction positioning portion 334 of the insertion seat 33 is removably limited by the limiting member 323 of the upper portion 302 of the main body assembly 300, so as to form a retraction limiting structure (B) (see FIG. 4) that positions the retraction seat 35 relative to the insertion seat 33.

The second elastic member 37 has two opposite ends respectively abutting against the insertion seat 33 and the retraction seat 35. In this embodiment, the second elastic member 37 may be configured as a pre-compressed spring.

The base 50 is separably positioned relative to the lower portion 303 of the main body assembly 300, and includes a base seat 51, and an adhesive pad 52 that is fixedly connected to the base seat 51. In one embodiment, the base 50 may further include a release layer 55 (see FIGS. 31 and 33) that is separably adhered to the adhesive pad 52.

The insertion module 30 further includes an auxiliary insertion seat 38 that is separably mounted to the insertion needle 36. The sensor assembly 70 is separably mounted to the auxiliary insertion seat 38. The auxiliary insertion seat 38 has a base portion 381, three angularly spaced-apart wing portions 382 each extending radially outwardly from the base portion 381, and a plurality of coupling portions 383 (see FIG. 3) that protrude from a bottom surface of the base portion 381. Each of the wing portions 382 has a plurality of notches 384, such that the wing portion 382 is flexible in a radial direction of the auxiliary insertion seat 38.

Referring to FIGS. 3 and 4, after first embodiment of the insertion device is assembled, the upper portion 302 and the lower portion 303 of the main body assembly 300 are interconnected, a top portion of the upper casing 10 and a top portion of the upper portion 302 of the main body assembly 300 are spaced apart from each other by a distance (D) (see FIG. 3), the buckle portions 335 of the insertion seat 33 respectively abut against the stopping portions 317 of the lower portion 303 of the main body assembly 300 so as to position the insertion seat 33 at a pre-insertion position, the first elastic member 34 is pre-compressed between the insertion seat 33 and the upper portion 302 of the main body assembly 300 to generate a restoring force, the second elastic member 37 is pre-compressed between the retraction seat 35 and the insertion seat 33 to generate a restoring force, the retraction seat 35 is at a pre-insertion position, the coupling portions 383 of the auxiliary insertion seat 38 is fitted into the coupling portion 711 of the sensing seat 71 so that the sensing seat 71 and the auxiliary insertion seat 38 are interconnected, the auxiliary insertion seat 38 is connected to a needle seat 361 of the insertion needle 36 so that the insertion needle 36 is retained in the lower portion 303 of the main body assembly 300 and is shielded by the base 50, and the base 50 is positioned relative to the lower portion 303 of the main body assembly 300.

Figure 5:
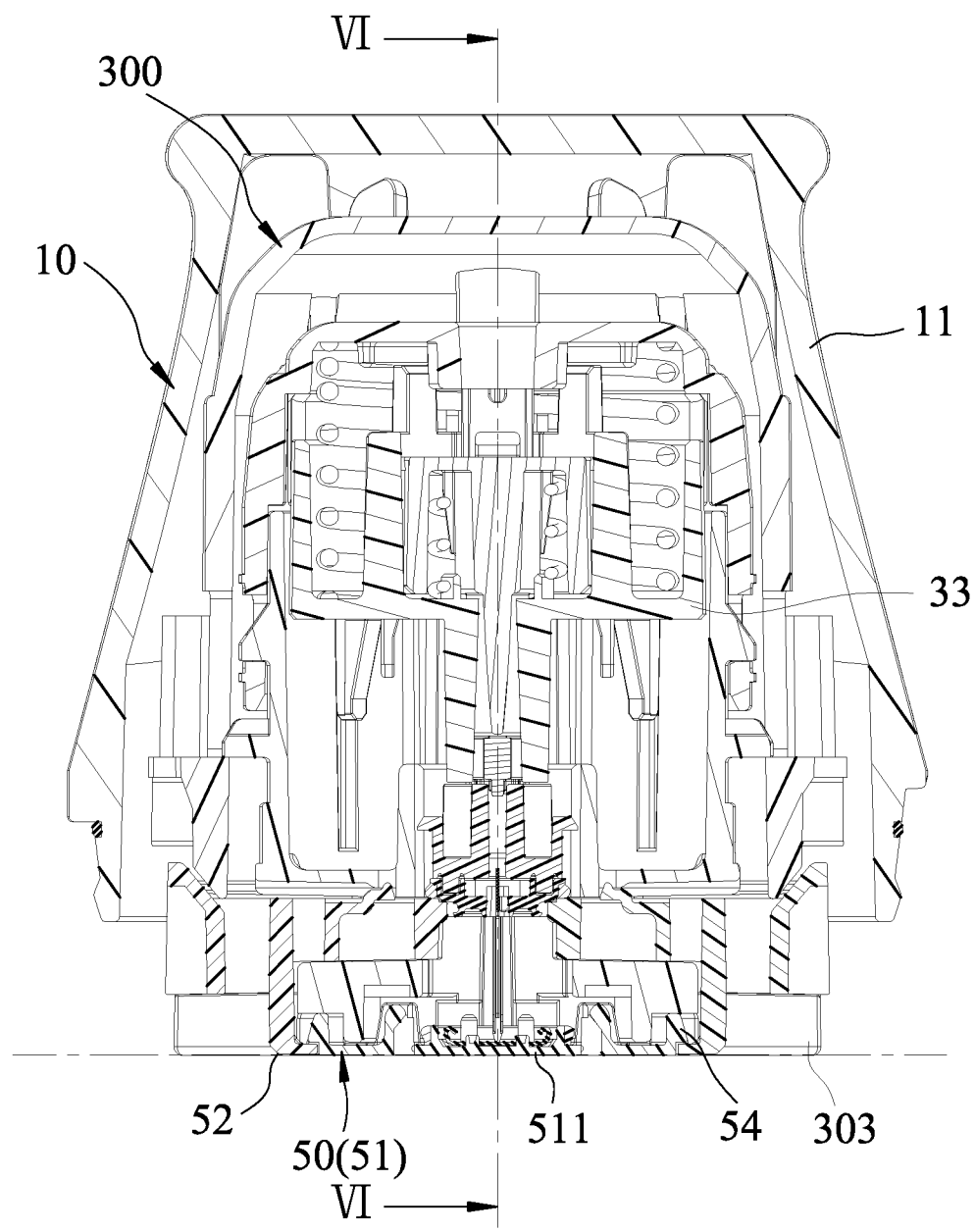
FIG. 5 is a sectional view illustrating a lower casing of the first embodiment uncovering a base.
Figure 6:
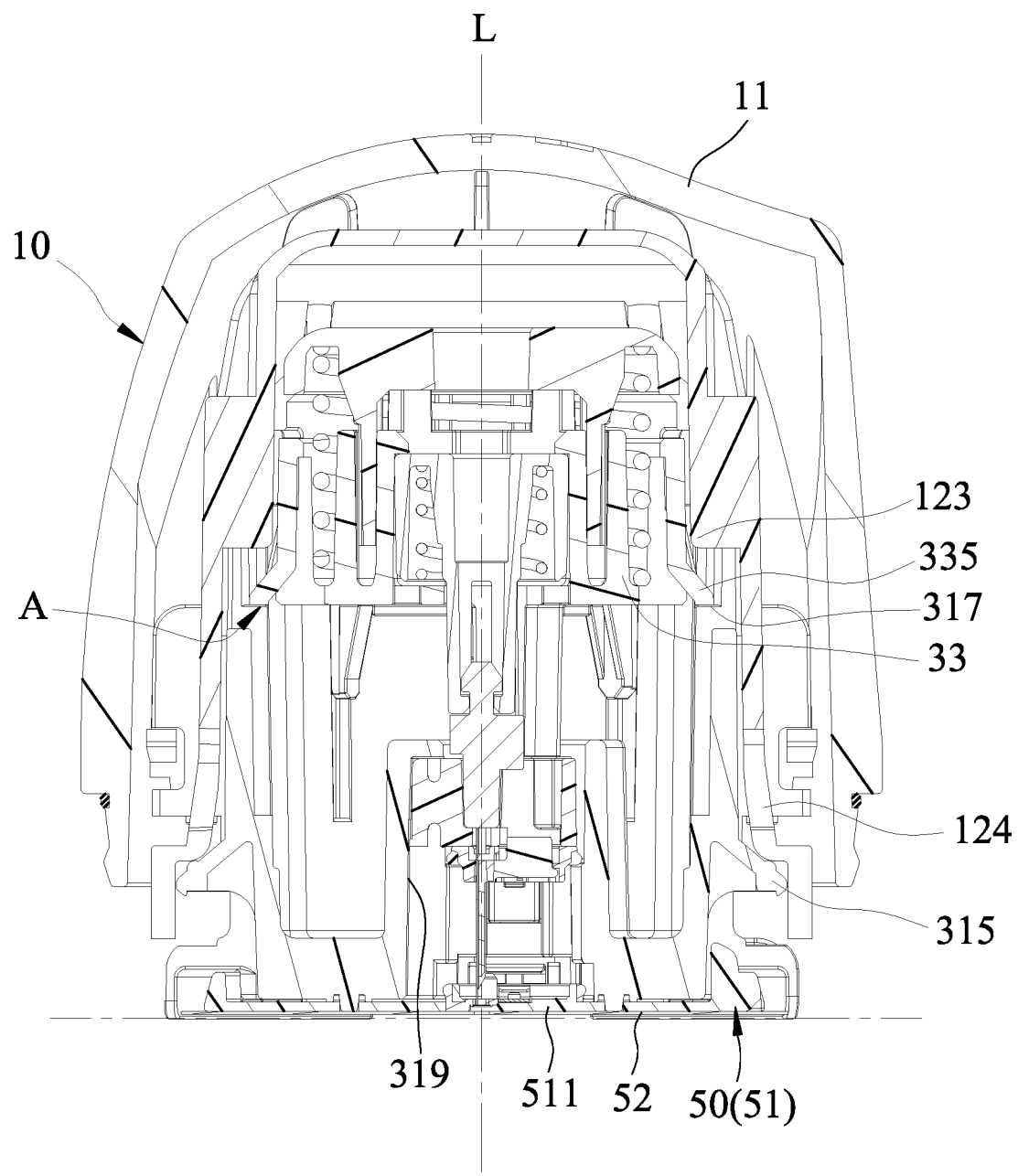
FIG. 6 is a sectional view taken along line VI-VI in FIG. 5.
Figure 7:
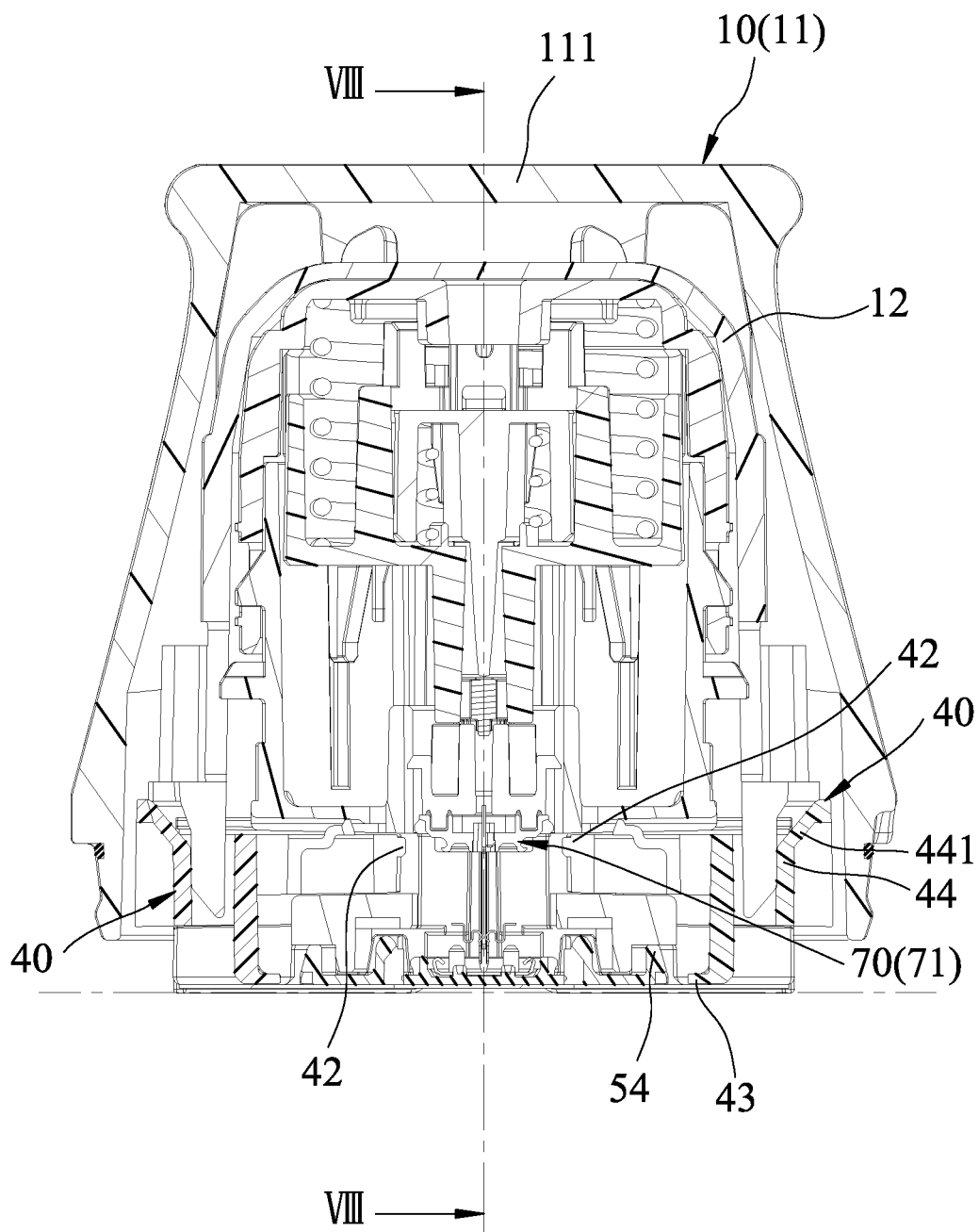
FIG. 7 is a sectional view illustrating an upper casing of the first embodiment being depressed.
Figure 8:
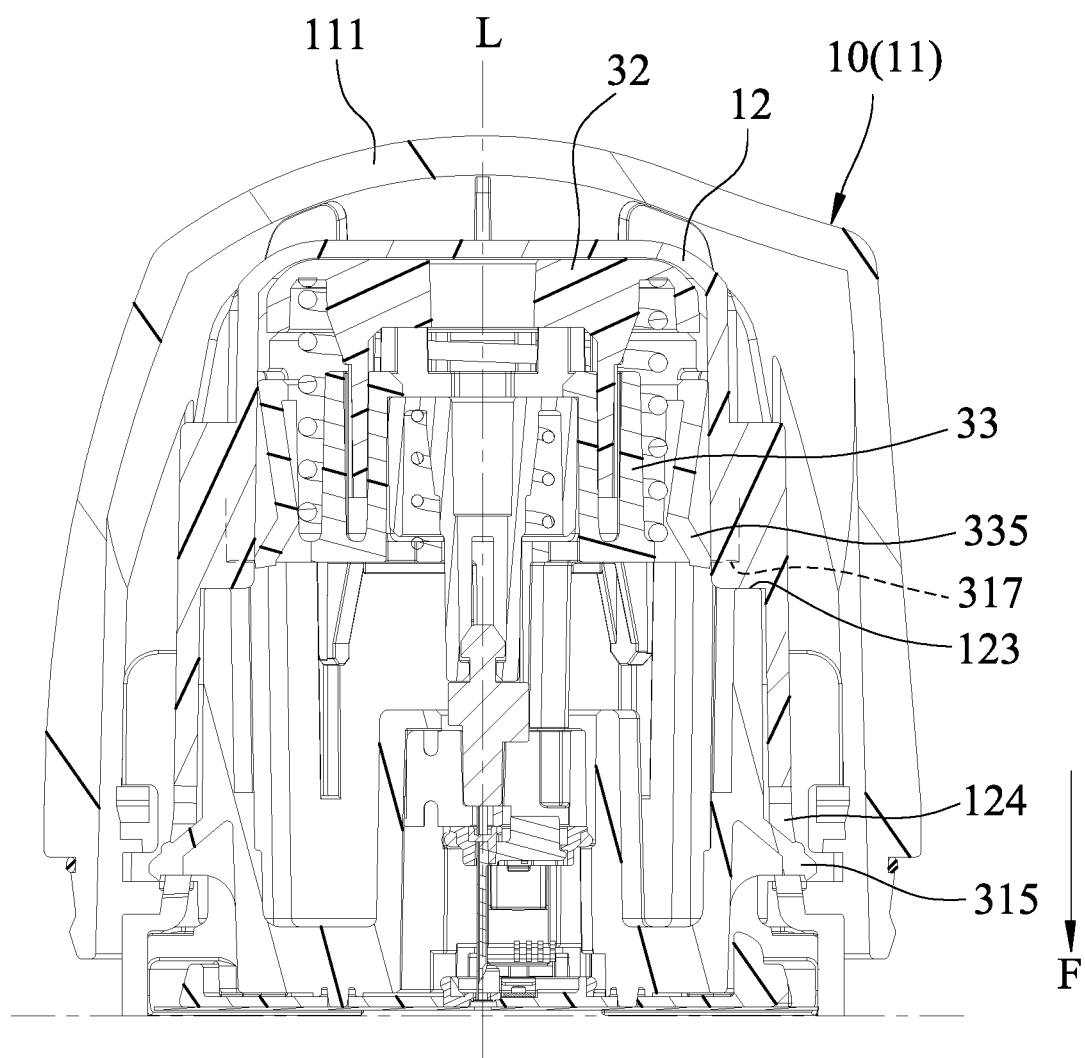
FIG. 8 is a sectional view taken along line VIII-VIII in FIG. 7.
Figure 9:
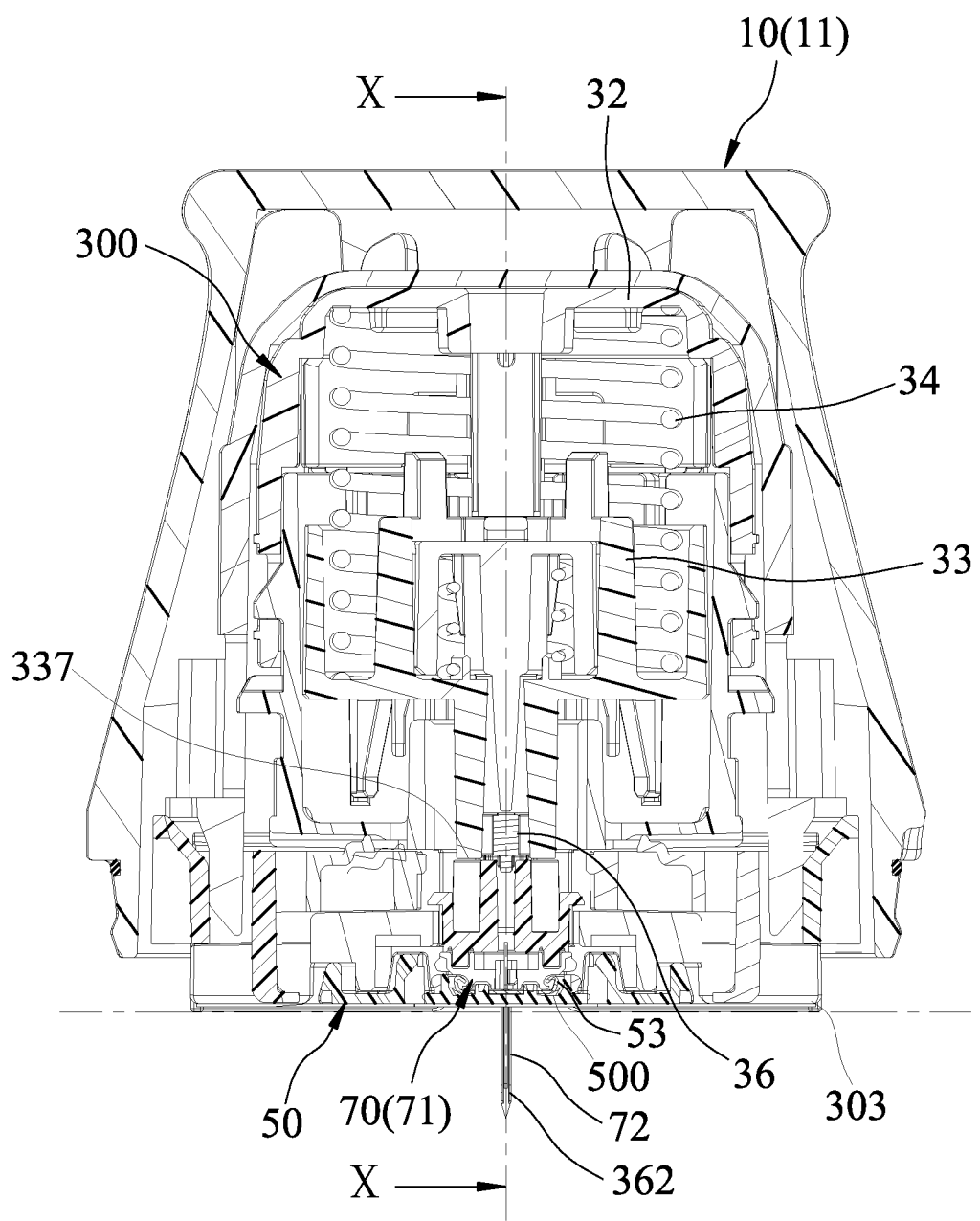
FIG. 9 is a sectional view illustrating an insertion seat of the first embodiment being moved toward a host.
Figure 10:
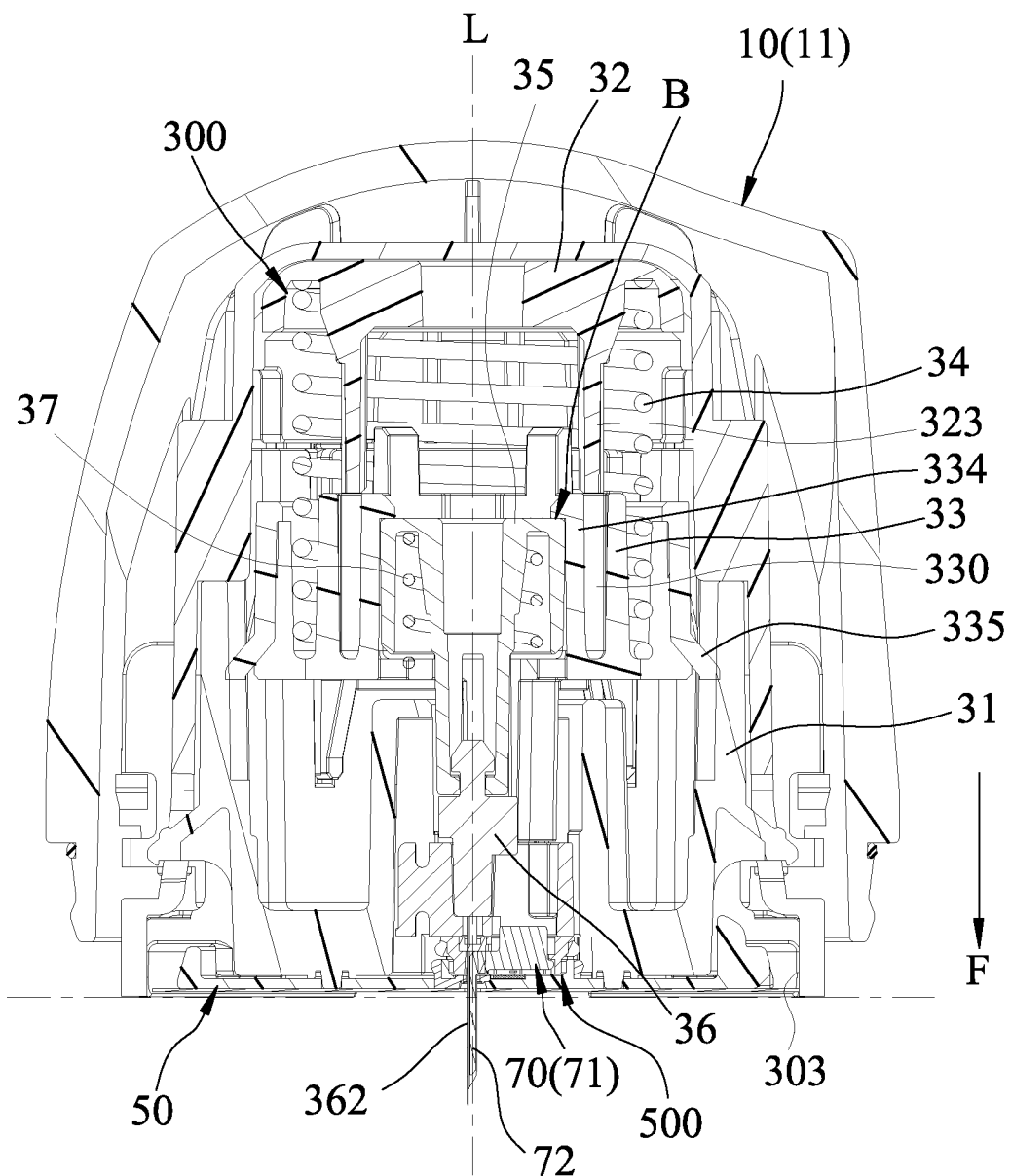
FIG. 10 is a sectional view taken along line X-X in FIG. 9.
Figure 11:
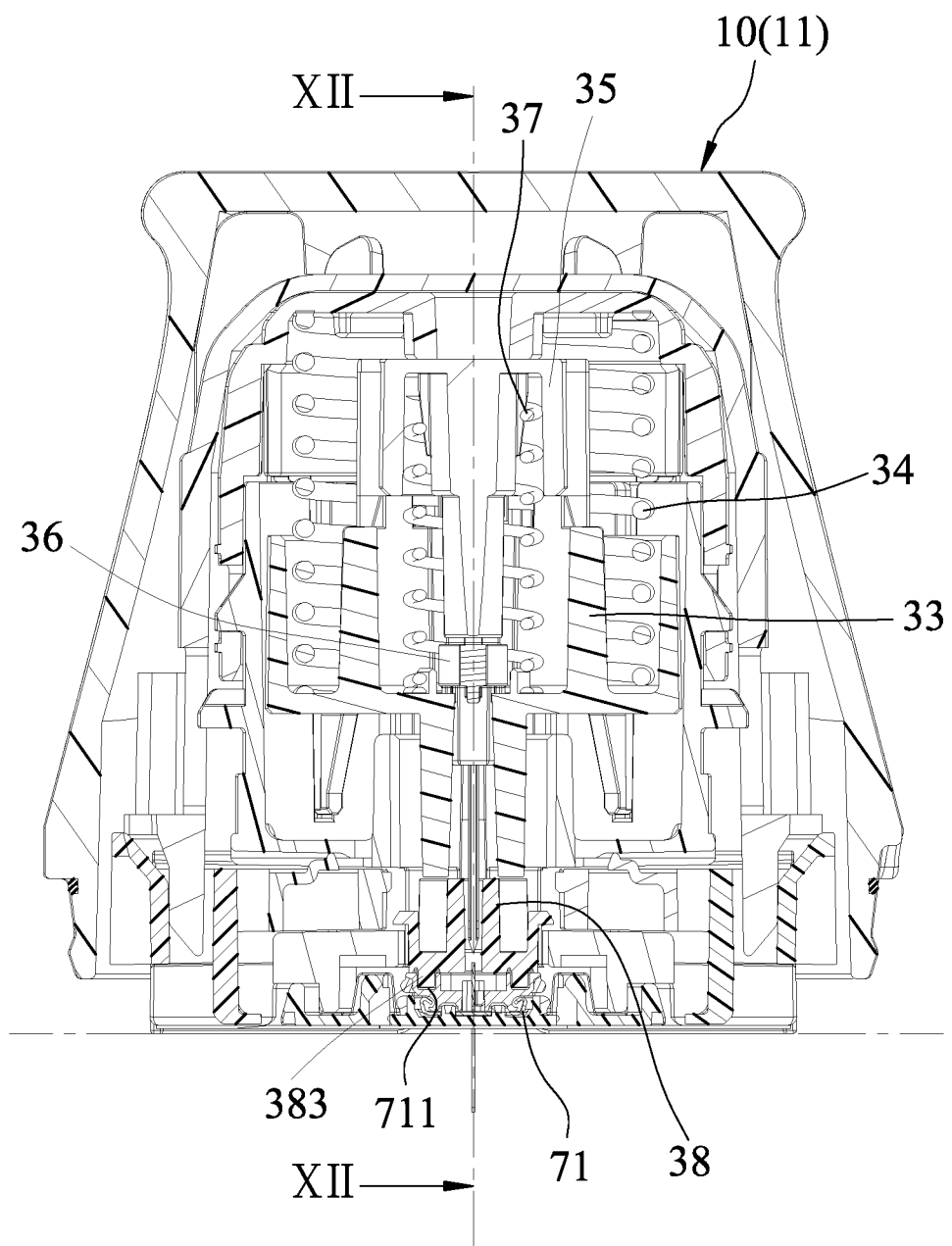
FIG. 11 is a sectional view illustrating a retraction seat of the first embodiment being moved away from the host.
Figure 12:
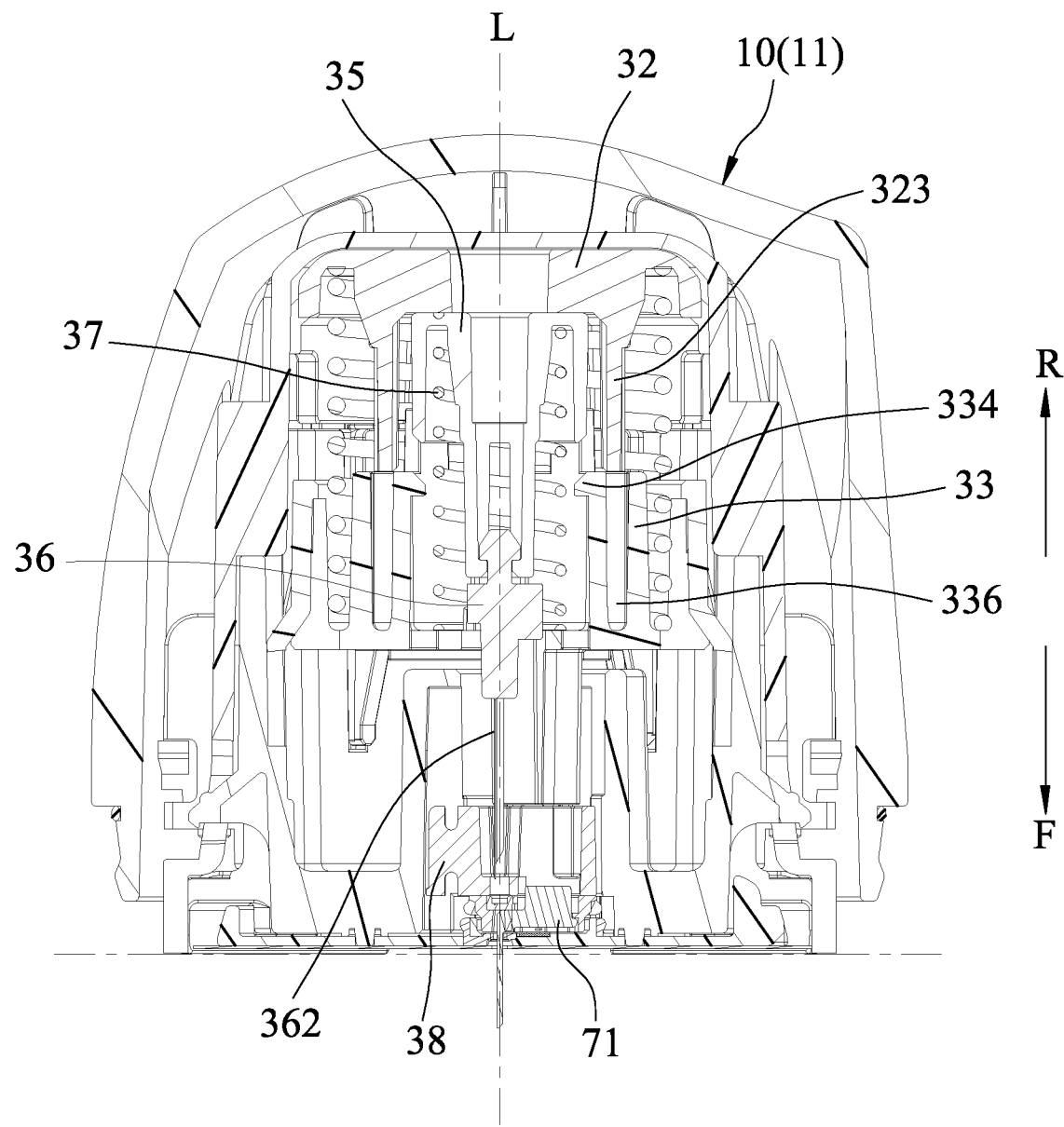
FIG. 12 is a sectional view taken along line XII-XII in FIG. 11.

The insertion operation performed by the first embodiment (to insert the sensor 72 into the host) is illustrated as follows:

Referring to FIGS. 5 and 6, the adhesive pad 52 is adhered to a skin surface of the host. Referring to FIGS. 7 and 8, when the upper casing 10 is not depressed, the insertion limiting structure (A) that is formed between the buckle portions 335 of the insertion seat 33 and the stopping portions 317 of the lower portion 303 of the main body assembly 300 maintains the insertion seat 33 at the pre-insertion position. When the upper casing 10 is depressed toward the skin surface, the buckle portions 335 of the insertion seat 33 are respectively pushed by the urging portions 123 of the upper casing 10 to be deformed inwardly and to be respectively separated from the stopping portions 317 of the lower portion 303 of the main body assembly 300, so that the insertion limiting structure (A) is collapsed. At the same time, the body engaging structures 315 of the main body assembly 300 respectively engage the casing engaging structure 124 of the upper casing 10, so that the upper casing 10 is positioned relative to the main body assembly 300. After the cover body 12 being pressed by the user, the actuating portions 123 (i.e., the urging portions 123) will be stuck underneath the main body 31, and thus the cover body 12 cannot be moved upward while the user does not feel any vibration nor noise Referring to FIGS. 9 and 10, after the insertion limiting structure (A) is collapsed, the restoring force of the first elastic member 34 is permitted to be released, and moves the insertion seat 33 to an insertion position to implement automatic-insertion, such that the sensor assembly 70 is moved by the insertion seat 33 to a post-insertion position, that a portion of the sensor 72 is inserted underneath the skin surface, and that the sensing seat 71 is positioned onto the mounting portion 500 of the base 50. After the sensor 72 is inserted underneath the skin surface, the limiting member 323 of the upper portion 302 of the main body assembly 300 is separated from the limiting groove 330 and the retraction positioning portion 334 of the insertion seat 33, so that the retraction positioning portion 334 is permitted to be deformed outwardly to collapse the retraction limiting structure (B). As such, the restoring force of the second elastic member 37 is permitted to be released, and drives the retraction seat 35 to move past the retraction positioning portion 334 of the insertion seat 33 away from the skin surface, such that the insertion needle 36 is separated from the auxiliary insertion seat 38 and is retracted into the insertion seat 33 to hide a needle 362 thereof and to implement automatic-retraction (see FIGS. 11 and 12). At this time, the coupling portions 383 of the auxiliary insertion seat 38 is maintained to be fitted into the coupling portion 711 of the sensing seat 71 so that the auxiliary insertion seat 38 is connected to the sensing seat 71 of the sensor assembly 70.

Figure 13:
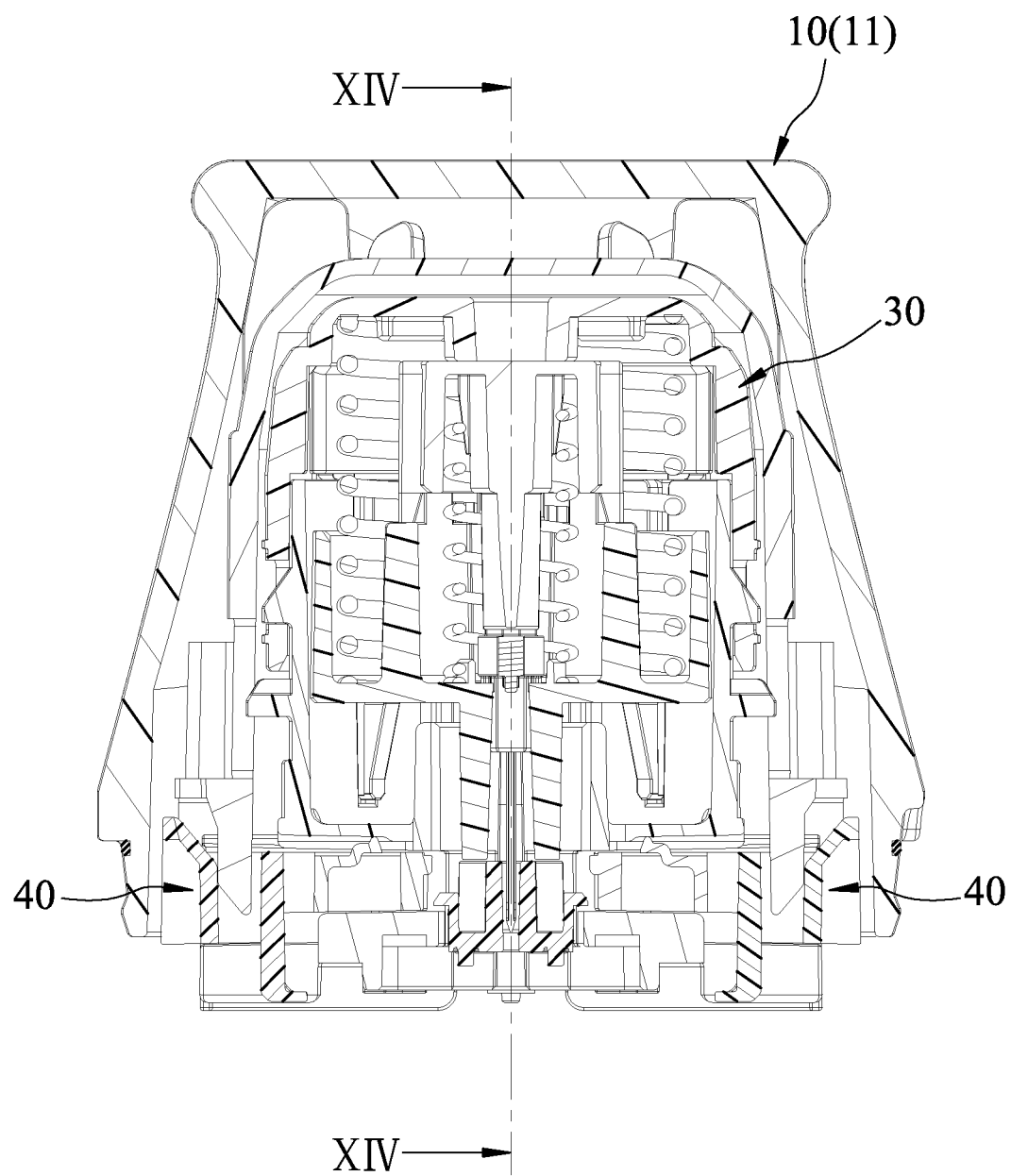
FIG. 13 is a sectional view illustrating an auxiliary insertion seat of the first embodiment being separated from a sensor assembly.
Figure 14:
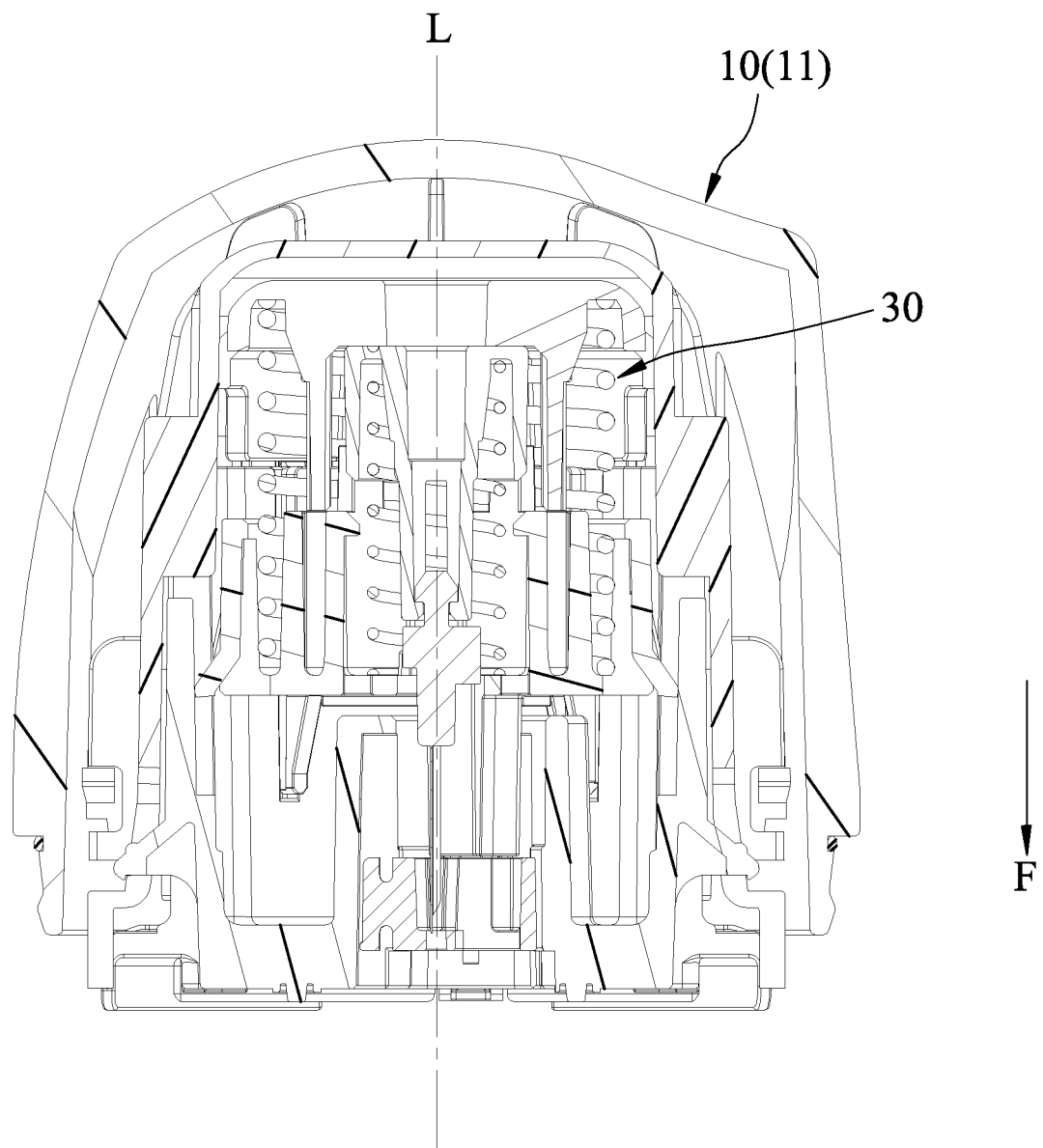
FIG. 14 is a sectional view taken along line XIV-XIV in FIG. 13.
Figure 28:
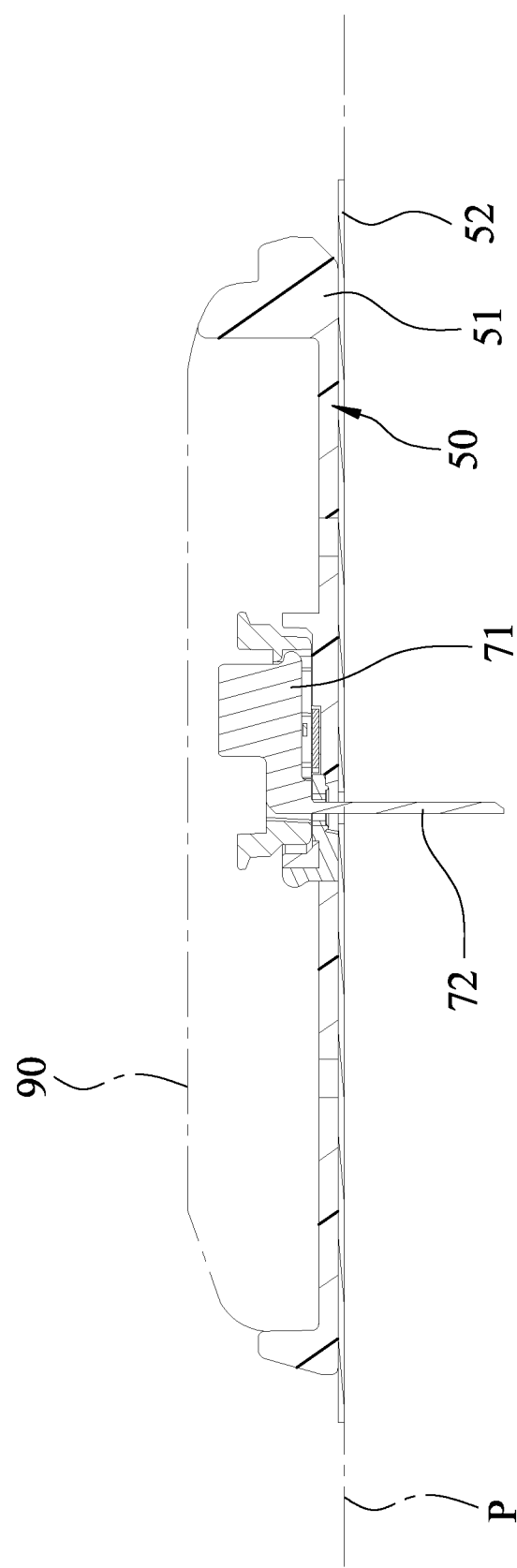
FIG. 28 is a sectional view illustrating a sensor assembly being mounted onto a base.

Afterward, the upper casing 10 and the insertion module 30 are separated from the base 50 and the skin surface of the host (the auxiliary insertion seat 38 is separated from the sensing seat 71 of the sensor assembly 70), so as to finish the insertion operation of the first embodiment of the insertion device including the automatic-insertion and automatic-retraction operations (see FIGS. 13, 14 and 28).

Accordingly, the first embodiment of the insertion device according to the disclosure is operated via a single-action operation. When the upper casing 10 is depressed, the insertion seat 33 is driven by the compressed first elastic member 34 to move toward the skin surface so as to perform the automatic-insertion operation and to separate the limiting structures (i.e., the limiting groove 330 and the limiting member 323) between the insertion seat 33 and the upper portion 302 of the main body assembly 300. After the automatic-insertion operation is done, the upper casing 10 is positioned relative to the main body assembly 300 without rebounding, and the limiting structures between the insertion seat 33 and the upper portion 302 are separated from each other, so that the retraction seat 35 is driven by the pre-compressed second elastic member 37 to perform the automatic-retraction operation. In this embodiment, a time needed for performing the automatic-insertion operation and the automatic-retraction operation is no more than 100 milliseconds. In other words, during the insertion operation of the first embodiment, the duration for which the insertion needle 36 is inserted into the host is no more than 100 milliseconds. In other embodiments, the duration may be no more than 50 milliseconds, no more than 8 milliseconds, no more than 6 milliseconds, no more than 4 milliseconds or no more than 2 milliseconds.

Referring back to FIGS. 1 to 4, a modification of the first embodiment of the insertion device according to the disclosure is for inserting a sensor into a host. The modification may also be in the form of a canister (e.g., a desiccant canister), but is not limited to such.

The modification of the insertion device includes an upper casing 10, a lower casing 20, an insertion module 30, a base 50 and a desiccant 60.

The upper casing 10 includes an outer shell 11, and a cover body 12 that is disposed in the outer shell 11. The cover body 12 has at least one casing engaging structure 124 at a lower portion thereof. The outer casing 11 has an annular protruding portion 115 and an upper positioning portion 116.

The lower casing 20 is separably and airtightly connected to the upper casing 10 so as to form an airtight space 200 (see FIG. 4) therebetween. The desiccant 60 is disposed in the airtight space 200.

In this modification, the upper casing 10 and the lower casing 20 are interconnected in a hard-interference manner, but are not limited to such. The lower casing 20 has a top edge 233. The top edge 233 of the lower casing 20 is provided with a lower positioning portion 227 that corresponds in position and shape to the upper positioning portion 116 of the upper casing 10. The lower casing 20 further has at least one abutment portion 228 at an inner surrounding surface thereof that abuts against an outer side of the casing engaging structure 124 of the upper casing 10, and an annular groove 224 at the inner surrounding surface thereof that permits the annular protruding portion 115 of the upper casing 10 to engage therewith so as to interconnect the upper casing 10 and the lower casing 20.

In this modification, the insertion device may further include a sealing ring 13 (see FIGS. 3 and 4) that is disposed between the annular protruding portion 115 of the upper casing 10 and the annular groove 224 of the lower casing 20 for enhancing air-tightness of the airtight space 200 defined between the upper casing 10 and the lower casing 20.

The insertion module 30 is disposed in the upper casing 10, and is able to be moved by the upper casing 10. The insertion module 30 includes a main body assembly 300. The main body assembly 300 includes a main body 31, and a main cover 32 that is connected to the main body 31 and that cooperates with the main body 31 to define a displacement space 301 therebetween. The main body assembly 300 further has at least one body engaging structure 315 that abuts against an inner side of the casing engaging structure 124 of the upper casing 10. The body engaging structure 315 engages with the casing engaging structure 124 of the upper casing 10 when the upper casing 10 is depressed.

In this modification, the body engaging structure 315 of the main body assembly 300 is disposed on the main body 31 of the main body assembly 300, and the body engaging structure 315 abuts against the inner side of the casing engaging structure 124 of the cover body 12 of the upper casing 10. When the lower casing 20 engages the upper casing 10, the abutment portion 228 of the lower casing 20 limits movement of the casing engaging structure 124 of the cover body 12 of the upper casing 10, such that the upper casing 10 cannot move downwardly so as to prevent unintentional insertion operation of the insertion device due to unintentionally applying force to the insertion device.

The insertion module 30 further includes an insertion seat 33 that is disposed in the displacement space 301, a first elastic member 34 that has two opposite ends respectively abutting against the insertion seat 33 and the main cover 32 for moving the insertion seat 33 in an insertion direction (F), a retraction seat 35 that is disposed in the insertion seat 33, an insertion needle 36 that is connected to the retraction seat 35, a second elastic member 37 that has two opposite ends respectively abutting against the insertion seat 33 and the retraction seat 35 for moving the retraction seat 35 in a retraction direction (R) opposite to the insertion direction (F), an auxiliary insertion seat 38 that is separably connected to the insertion needle 36, and a sensor assembly 70 that is separably connected to the auxiliary insertion seat 38. The sensor assembly 70 includes a sensing seat 71, and a sensor 72 that is mounted to the sensing seat 71 and that is separably coupled to the insertion needle 36.

In this modification, the first elastic member 34 and the second elastic 37 are configured as pre-compressed springs.

The cover body 12 of the upper casing 10 has a pair of urging portions 123 at an inner surrounding surface thereof. The insertion seat 33 has a pair of buckle portions 335 (see FIG. 4) that respectively and separably abut against two stopping portions 317 of the main body 31, and that are able to be respectively pushed by the urging portions 123 of the cover body 12 to be respectively separated from the stopping portions 317 of the main body 31. The buckle portions 335 of the insertion seat 33 respectively and separably abut the stopping portions 317 of the main body 31 so as to form an insertion limiting structure (A) between the insertion seat 33 and the main body 31.

The insertion seat 33 further has at least one limiting groove 330. The main cover 32 has at least one limiting member 323 that removably engages with the limiting groove 330 of the insertion seat 33. The insertion seat 33 further has at least one retraction positioning portion 334 that separably abuts against the limiting member 323 of the main cover 32 and that limits movements of the retraction seat 35. The retraction positioning portion 334 of the insertion seat 33 is limited by the limiting member 323 of the main cover 32, so as to form a retraction limiting structure (B) among the retraction seat 35, the insertion seat 33 and the main cover 32 of the main body assembly 300.

In this embodiment, the sensor assembly 70 is to be separably mounted to the base 50, and includes a sensing seat 71, and a sensor 72 that is mounted to the sensing seat 71 and that is separably coupled to the insertion needle 36. The sensing seat 71 has a coupling portion 711 (see FIG. 3).

The base 50 is separably positioned relative to the main body 32 of the main body assembly 300, and permits the sensor assembly 70 to be mounted thereon after the sensor assembly 70 is separated from the auxiliary insertion seat 38. The base 50 includes a base seat 51, an adhesive pad 52 that is fixedly connected to the base seat 51, and two base hook structures 54 (see FIG. 3). In one embodiment, the base 50 may further include a release layer 55 (see FIGS. 31 and 33) that is separably adhered to the adhesive pad 52. The base 50 further has a mounting portion 500 (see FIG. 4) for the sensor assembly 70 to be separably mounted thereto. In this modification, the mounting portion 500 of the base 50 includes a recess 501 that permits the sensor assembly 70 to be press-fitted thereinto, or may include an adhesive layer 502 (e.g., double-sided tape) that is disposed in the recess 501 (see FIG. 31), or at least one resilient hook 503 (see FIG. 32) that is for engaging with the sensor assembly 70.

In this modification, the insertion device further includes a pair of fixing members 40. The fixing members 40 are mounted to a slide groove 310 (see FIG. 2) of the main body 31 of the main body assembly 300. Each of the fixing members 40 has a push portion 41 that corresponds in position to a respective one of two stop portions 226 (see FIG. 3) of the lower casing 20, a support portion 42 that is opposite to the push portion 41, a fixing hook structure 43 that is located between the push portion 41 and the support portion 42, and a cam portion 44 that is located between the push portion 41 and the support portion 42 and that has an inclined cam surface 441.

The push portion 41 of each of the fixing members 40 is limited by the respective one of the stop portions 226 of the lower casing 20, so that the fixing members 40 are positioned relative to the main body 31. The sensing seat 71 of the sensor assembly 70 is supported by the support portions 42 of the fixing members 40 so as to be positioned relative to the main body 31. The fixing hook structures 43 of the fixing members 40 respectively engage with the base hook structures 54 of the base 50.

With reference to FIGS. 3 and 4, before the lower casing 20 is separated from the upper casing 10, the fixing members 40 interfere with the lower casing 20 and the cover body 12 of the upper casing 10, so that the upper casing 10 is prevented from moving downwardly by the fixing members 40 to further prevent unintentional insertion operation of the insertion device.

Since the sensor assembly 70 has a lower end supported by the fixing members 40, and since the fixing members 40 engage with the base 50, the base 50 is limited within the insertion device. When the lower casing 20 is separated from the upper casing 10 (or uncovers the base 50 while being connected to the upper casing 10, in a modification), the upper casing 10 is permitted to be depressed, such that the cover body 12 moves downwardly to push and move the fixing member 40 laterally and outwardly so as to collapse the limiting structure among the fixing members 40, the sensor assembly 70 and the base 50. As such, the first elastic member 34 of the insertion module 30 is permitted to release the restoring force thereof to insert the insertion needle 36 and the sensor 72 of the sensor assembly 70 underneath the skin surface of the host, and the second elastic member 37 of the insertion module 30 is permitted to release the restoring force thereof to retract the insertion needle 36 to finish automatic-insertion and automatic-retraction operations.

Figure 22:
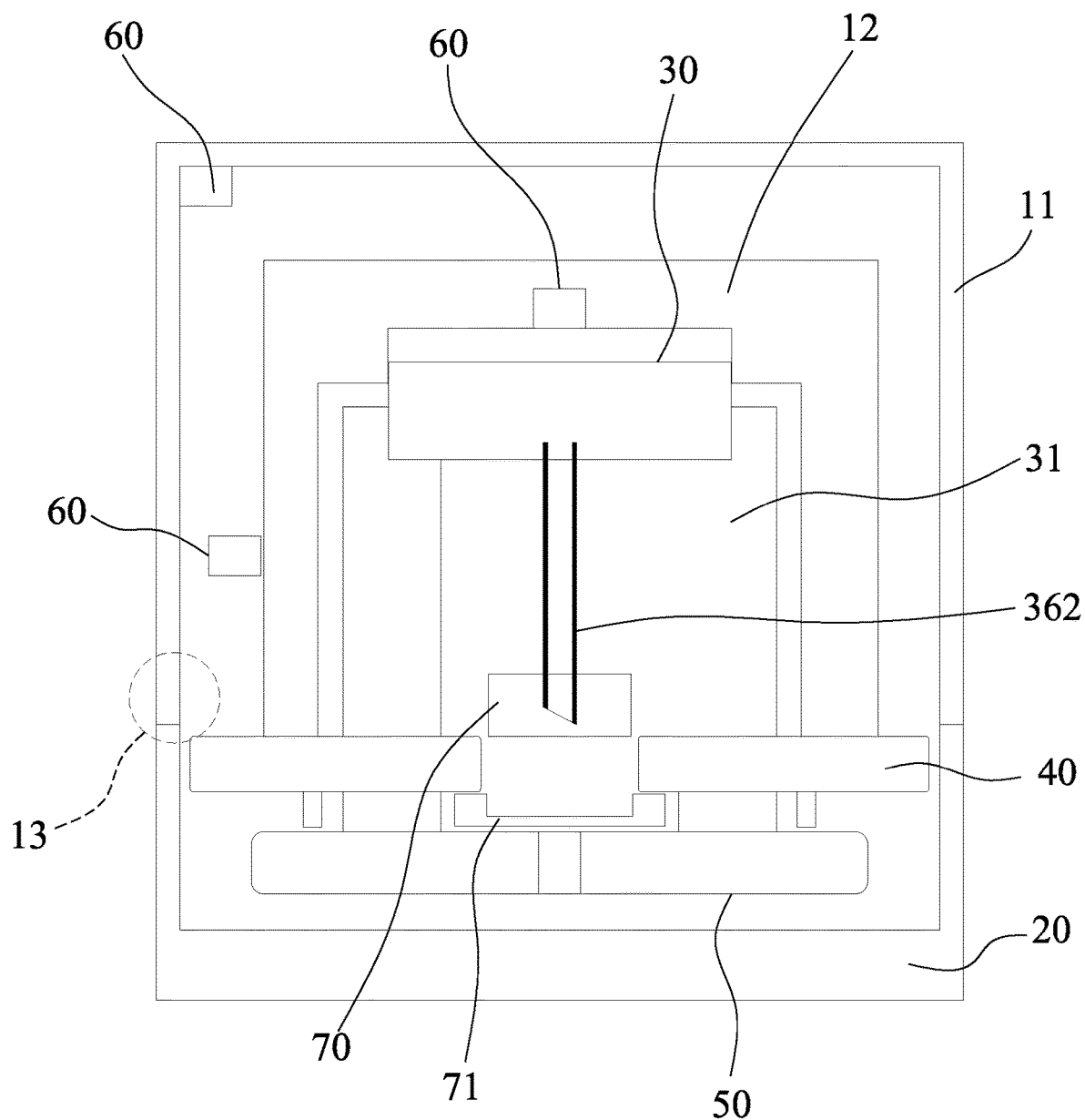
FIG. 22 is a schematic views illustrating a second embodiment of the insertion device according to the disclosure being assembled.
Figure 23:
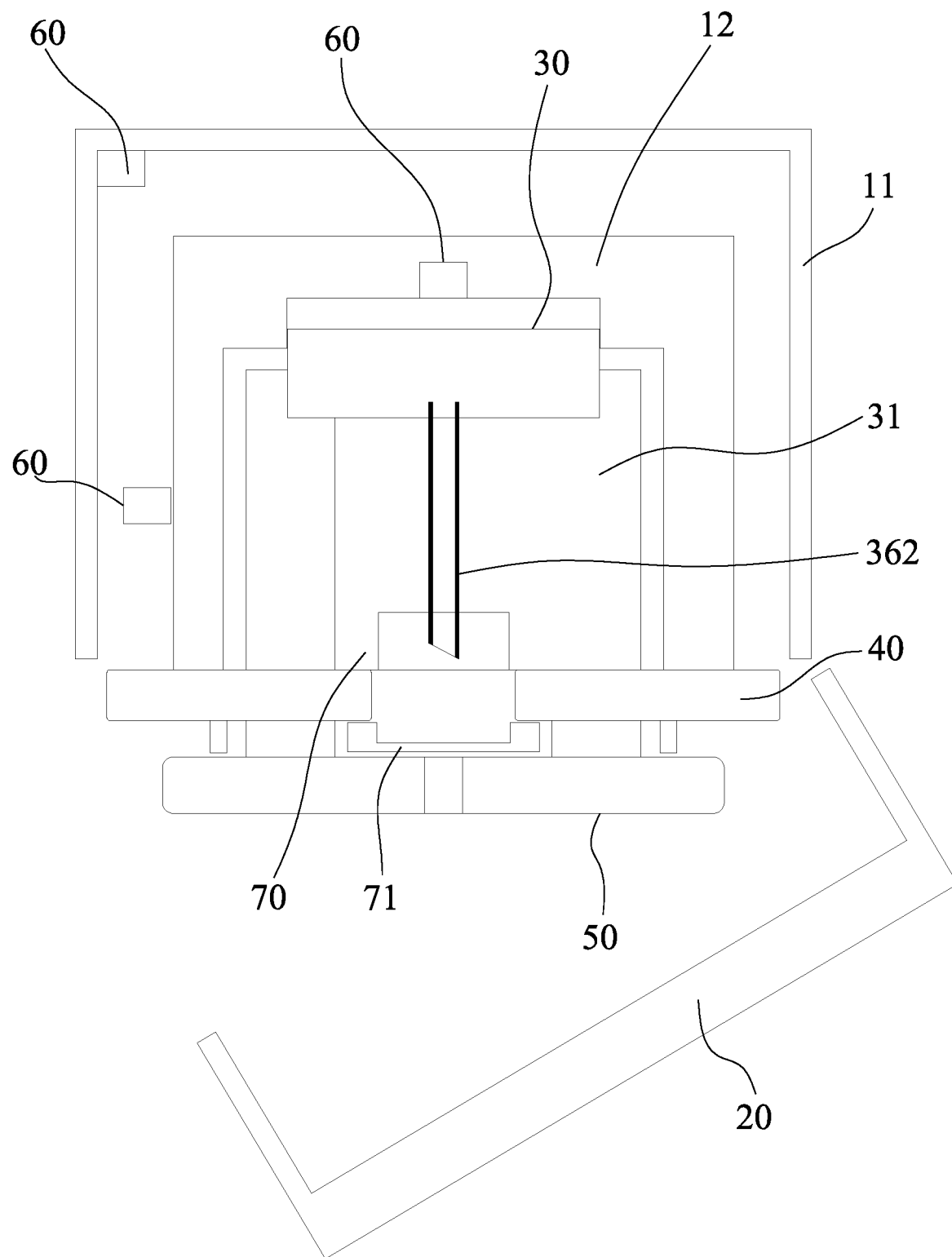
FIG. 23 is a schematic view illustrating a lower casing of the second embodiment uncovering a base.
Figure 24:
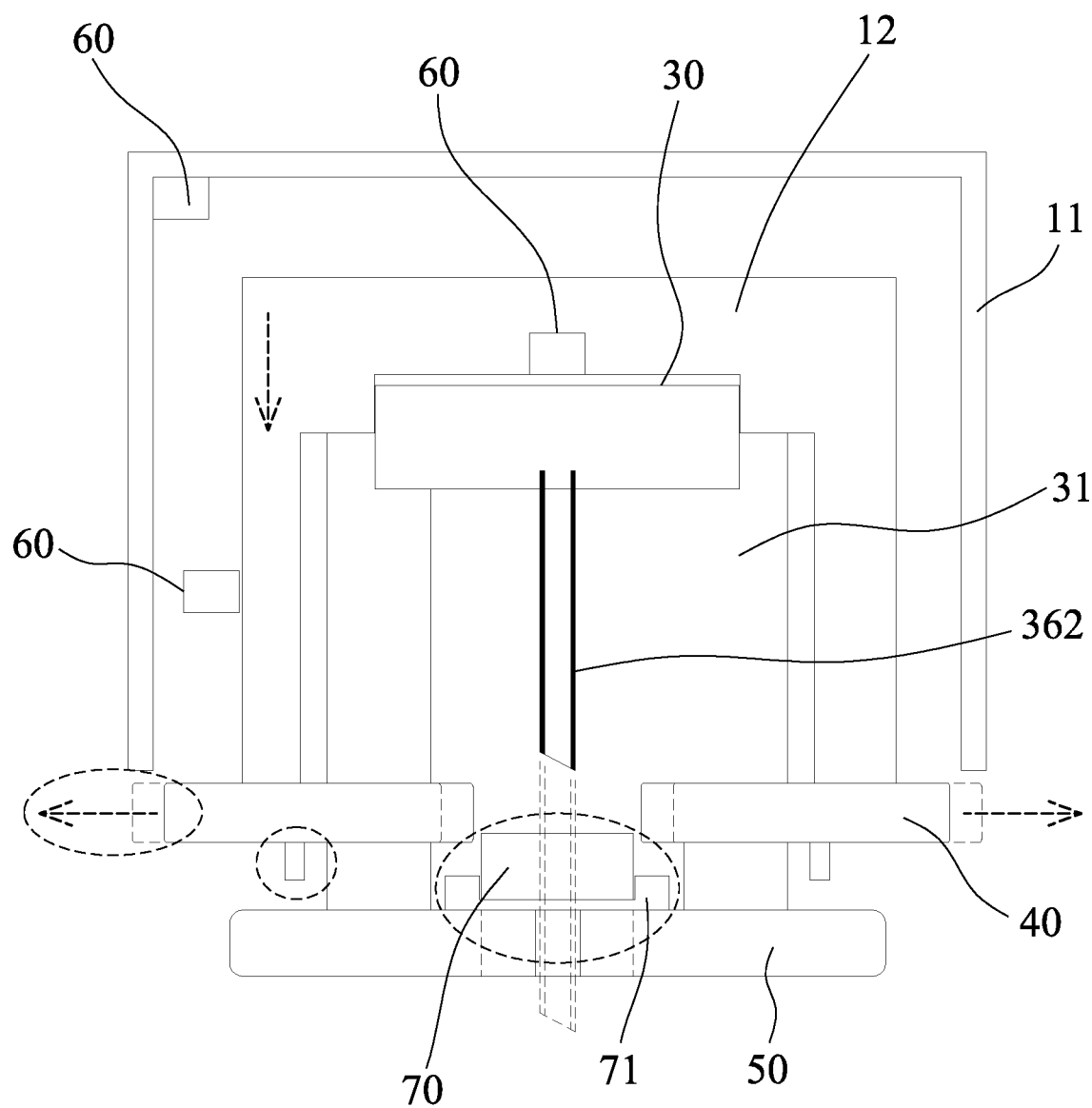
FIG. 24 is a schematic view illustrating operation of an insertion module.

Referring to FIGS. 3, 4, and 22 to 26 (FIGS. 22 to 26 are schematic views), a second embodiment, or a modification of the first embodiment of the insertion device according to the disclosure, is for inserting a sensor into a host. The outer shell 11 and the lower casing 20 (or the upper casing 20 and the lower casing 20) are airtightly coupled to each other, so that an inner space of the insertion device is airtight. The desiccant 60 may be disposed at a suitable position anywhere in the inner space of the insertion device. In another modification, any one of the components of the insertion module 30 may be made of materials including desiccant through an injection molding technology (as shown in FIGS. 22 and 23). In still another modification, an inner surface of the outer shell 11 may be provided with a desiccant layer 62 (see FIGS. 25 and 26), or the sensor assembly 70 may have a desiccant 60 (not shown) so that the inner space of the insertion device is kept dry and that the sensor assembly 70 is prevented from being moistened.

Figure 25:
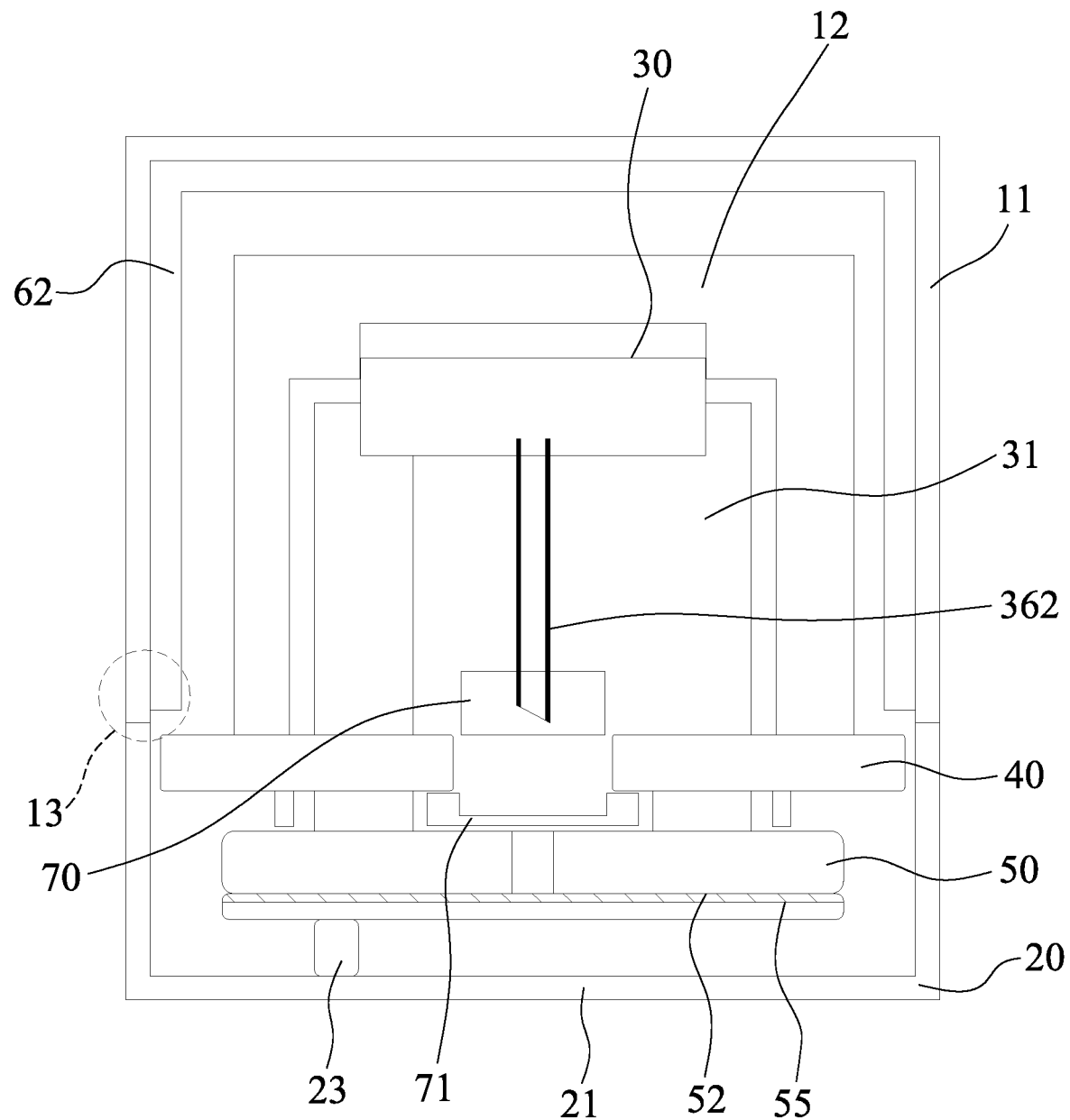
FIG. 25 is a schematic view illustrating the lower casing covering the base.
Figure 26:
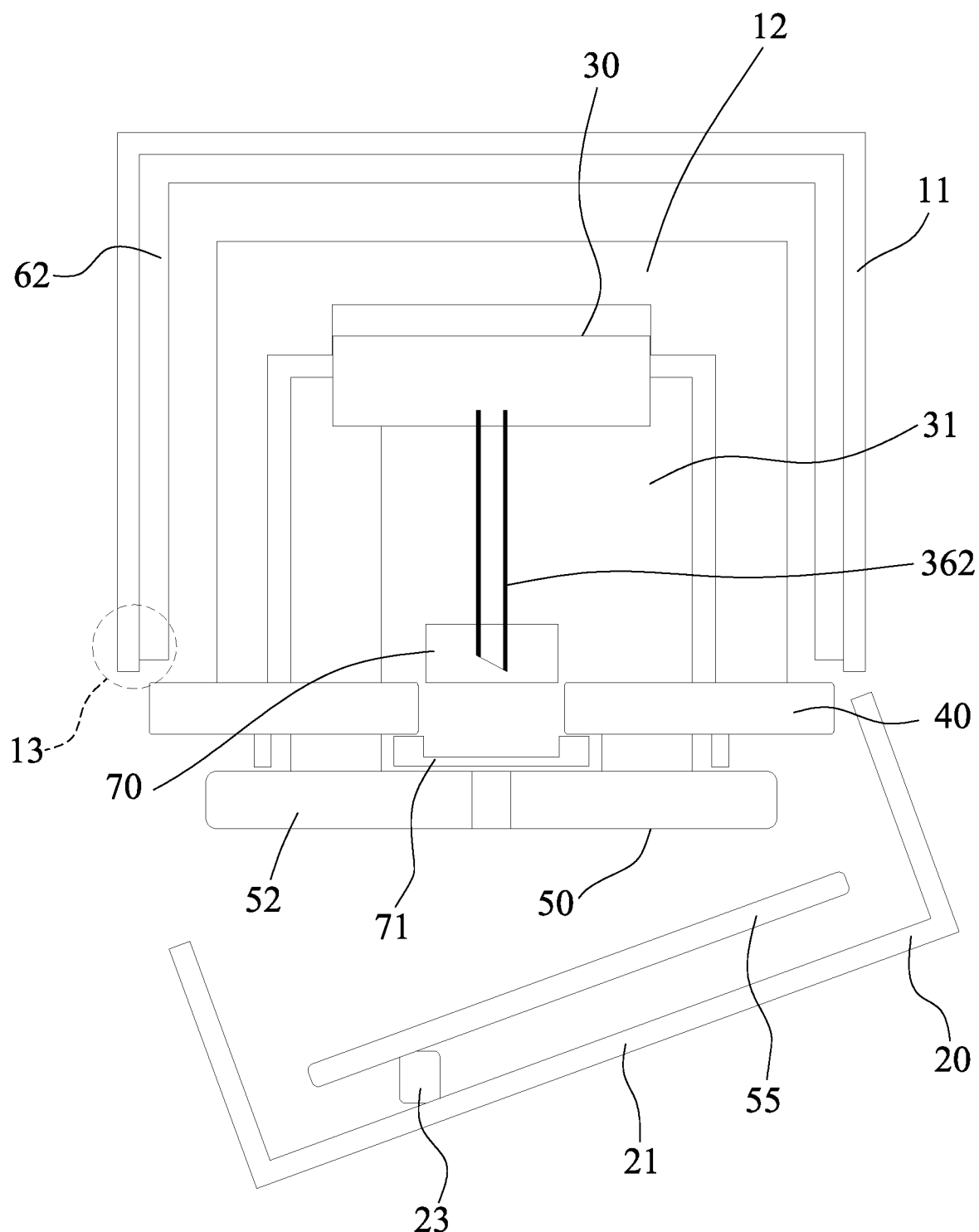
FIG. 26 is a schematic view illustrating the lower casing tearing a release layer via a tearing element when the lower casing uncovers the base.

Referring further to FIGS. 25 and 26, the base 50 further includes a tearing element 23 that is fixedly mounted to a base plate 21 of the lower casing 20. The tearing element 23 is connected to the release layer 55 (see FIGS. 31 and 33) that is separably adhered to the adhesive pad 52. When the lower casing 20 is separated from the upper casing 10 (or uncovers the base 50 while being connected to the upper casing 10), the tearing element 23 simultaneously separates the release layer 55 from the adhesive pad 52. Since the release layer 55 is not separated from the adhesive pad 52 until the insertion device is to perform the insertion operation, the adhesive pad 52 is prevented from being stained before the insertion operation. In this embodiment, the lower casing 20 is in the form of a cap. In other embodiments, the lower casing 20 may be in the form of an aluminum foil (not shown).

Figure 29:
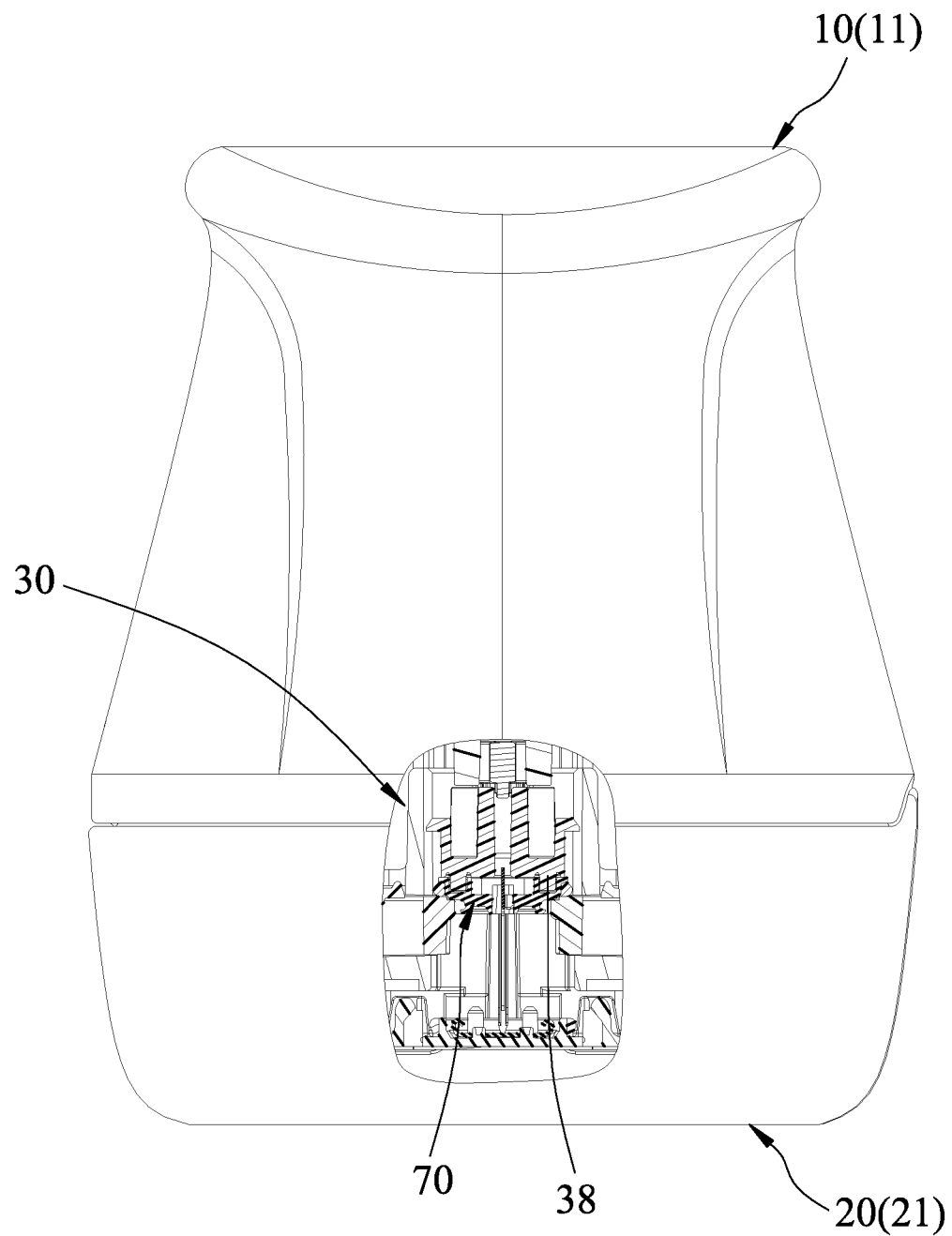
FIG. 29 is a partly sectional view illustrating the sensor assembly being connected to an auxiliary insertion seat.
Figure 30:
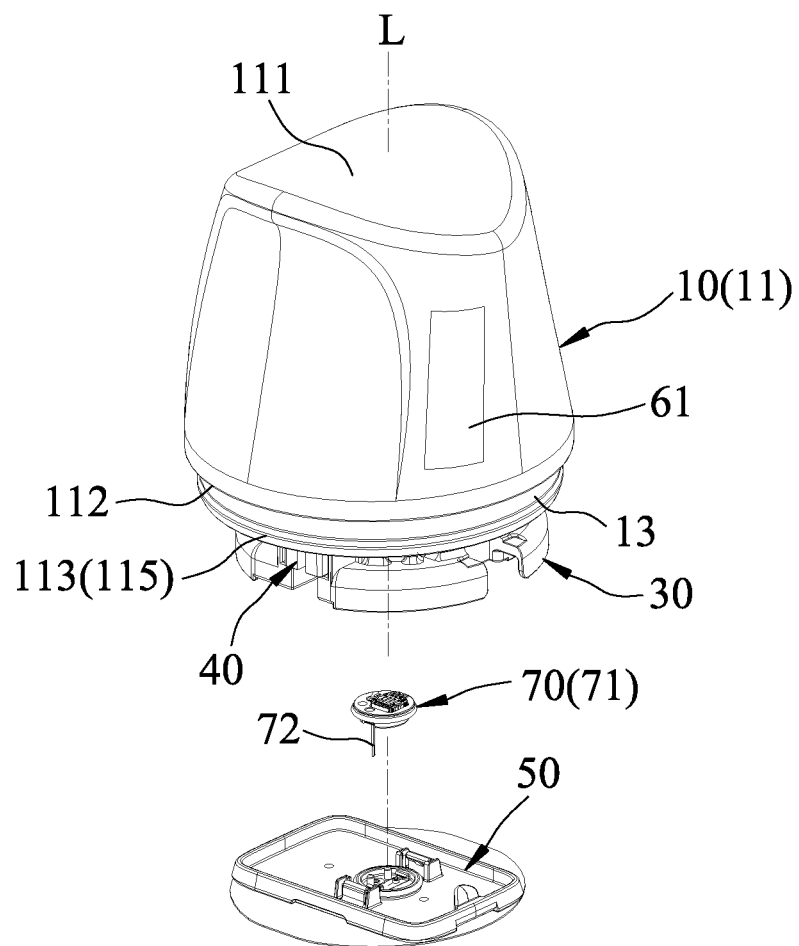
FIG. 30 is another exploded perspective view of the insertion device.

Referring to FIGS. 3 and 4, the outer shell 11 is sleeved onto the insertion module 30 after the components of the insertion module 30 are assembled. At this time, the sensor assembly 70 has been mounted to the insertion module 30 via the auxiliary insertion seat 38 (see FIG. 29), the lower casing 20 is subsequently coupled to the outer shell 11. The sensor assembly 70 does not need to be manually adjusted during the insertion operation of the insertion device. It means that a user does not require additional manual operation of grasping the sensor assembly 70 onto the base 50 by the implanting module 30 (i.e., the insertion module 30). In this embodiment, all the components of the insertion device have been assembled in the factory, but can be disassembled and reassembled by medical personnel or a user (see FIG. 30). When the insertion device is used to perform the insertion operation, the user can easily manipulate the insertion device (e.g., by simply depressing the upper casing 10) to mount the base 50 onto the skin surface of the host by the adhesive pad 52 of the base 50 followed by coupling the sensor assembly 70 onto the base 50.

Figure 15:
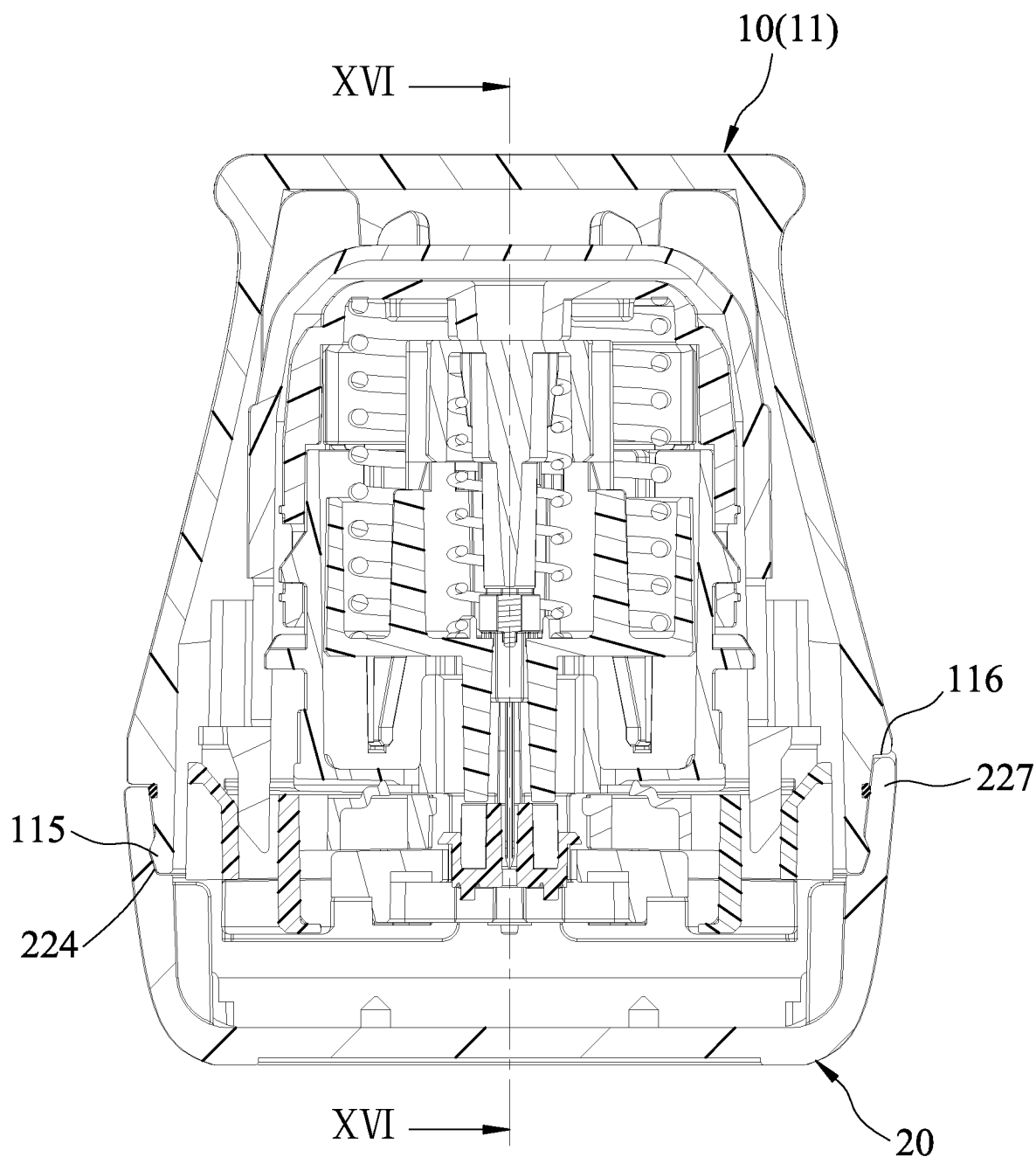
FIG. 15 is a sectional view illustrating the lower casing being re-coupled to the upper casing.
Figure 16:
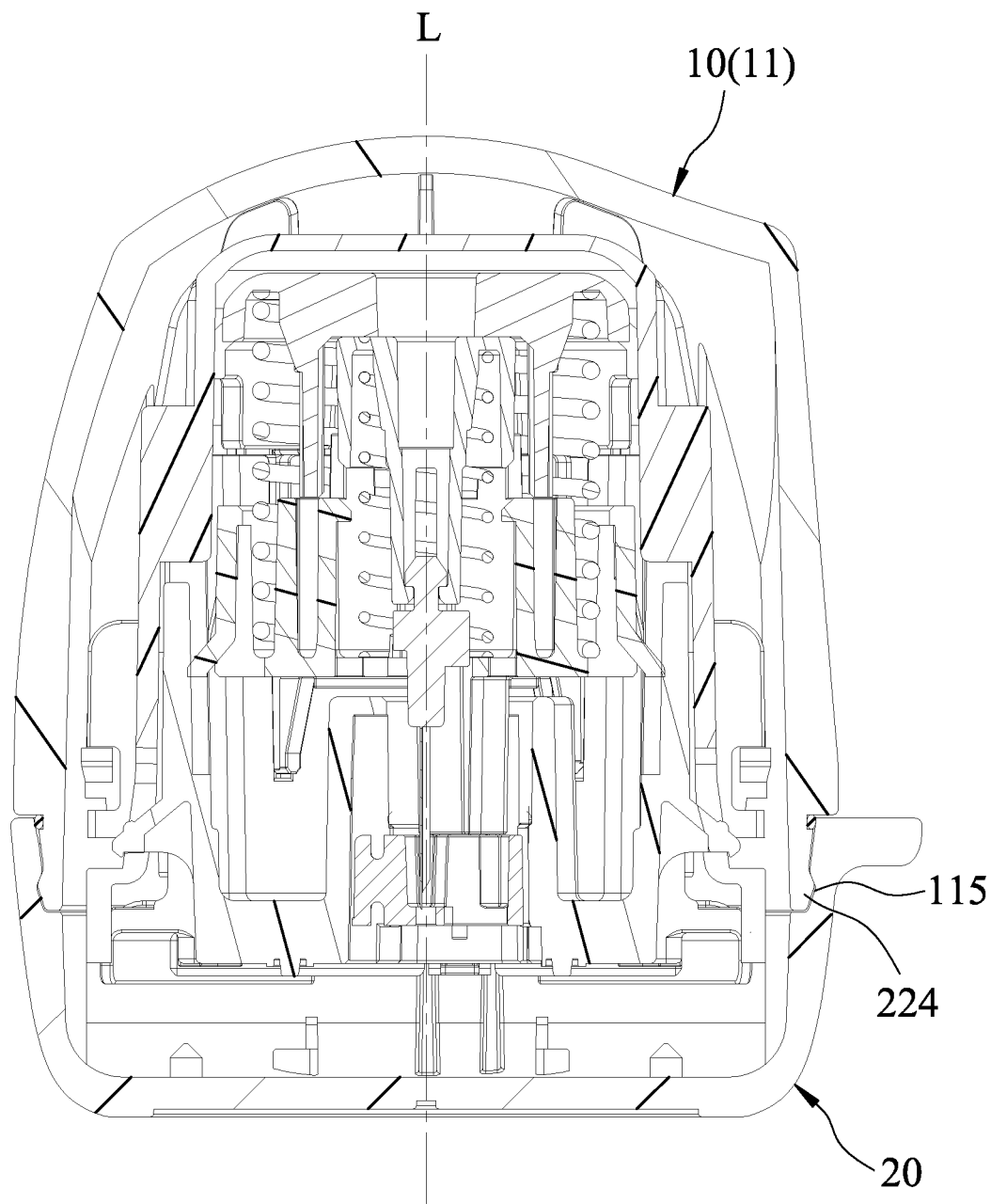
FIG. 16 is a sectional view taken along line XVI-XVI in FIG. 15.
Figure 17:
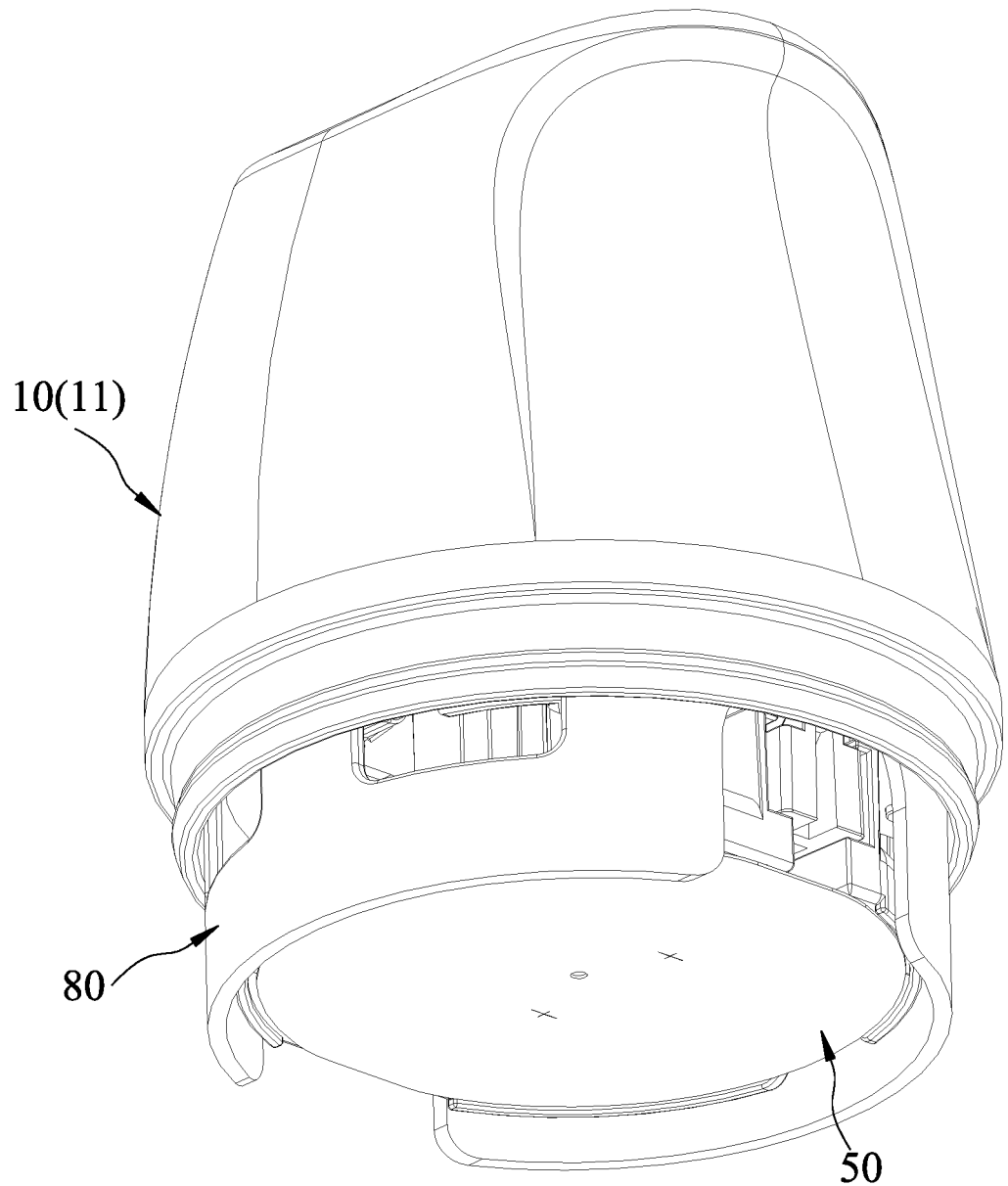
FIG. 17 is a perspective view illustrating a modification of the insertion device.
Figure 18:
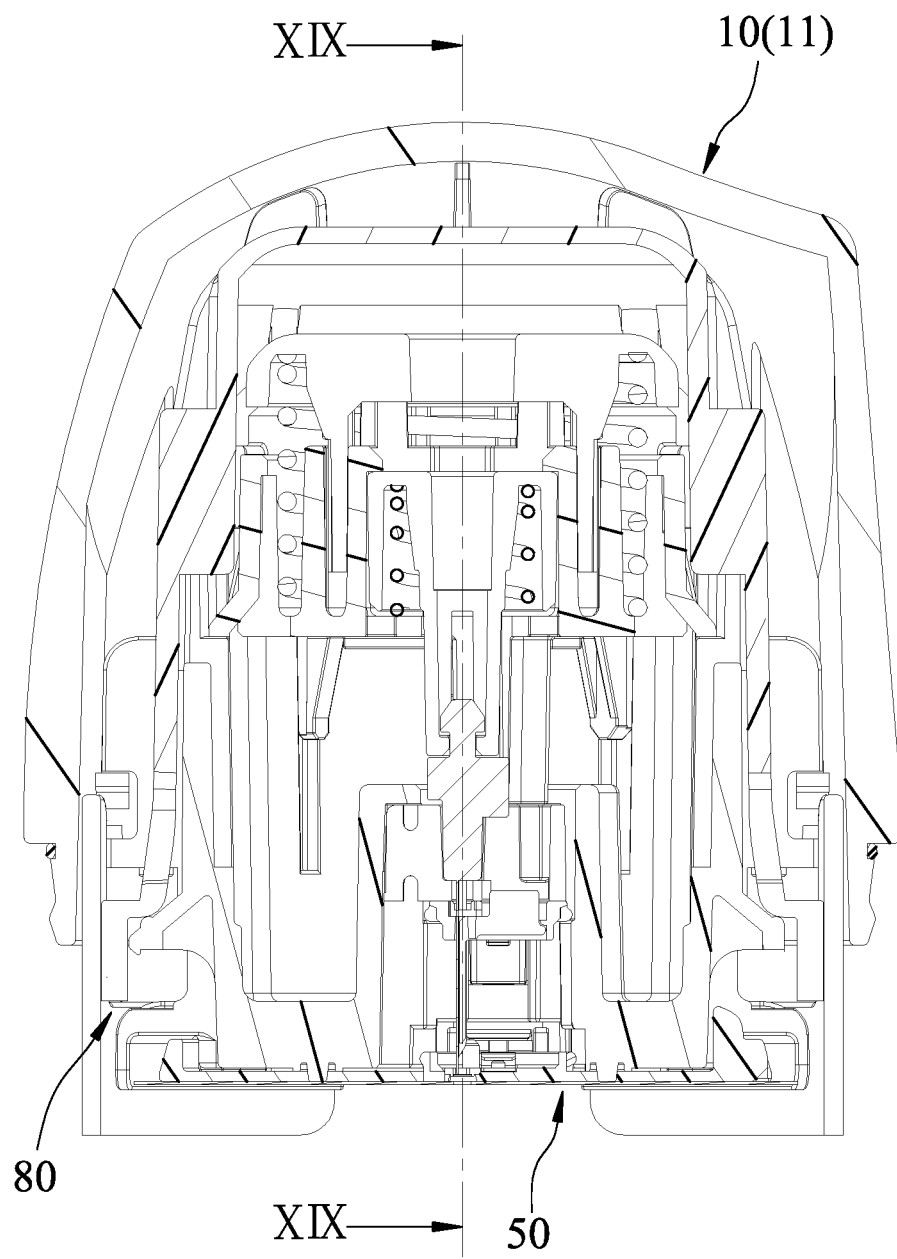
FIG. 18 is a sectional view of the modification shown in FIG. 17, illustrating a stage of being prepared for the implanting.
Figure 19:
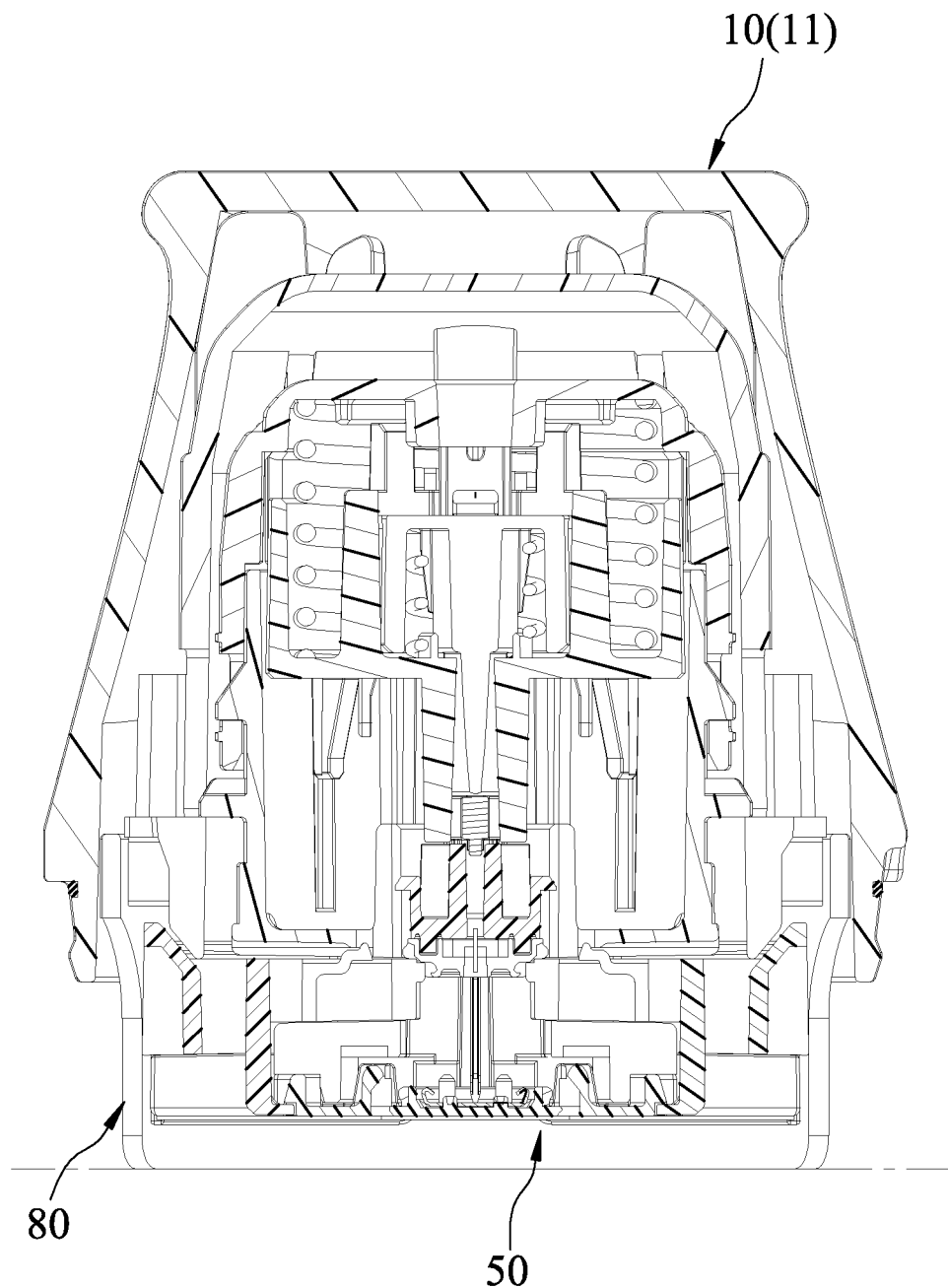
FIG. 19 is a sectional view taken along line XIX-XIX in FIG. 18.
Figure 20:
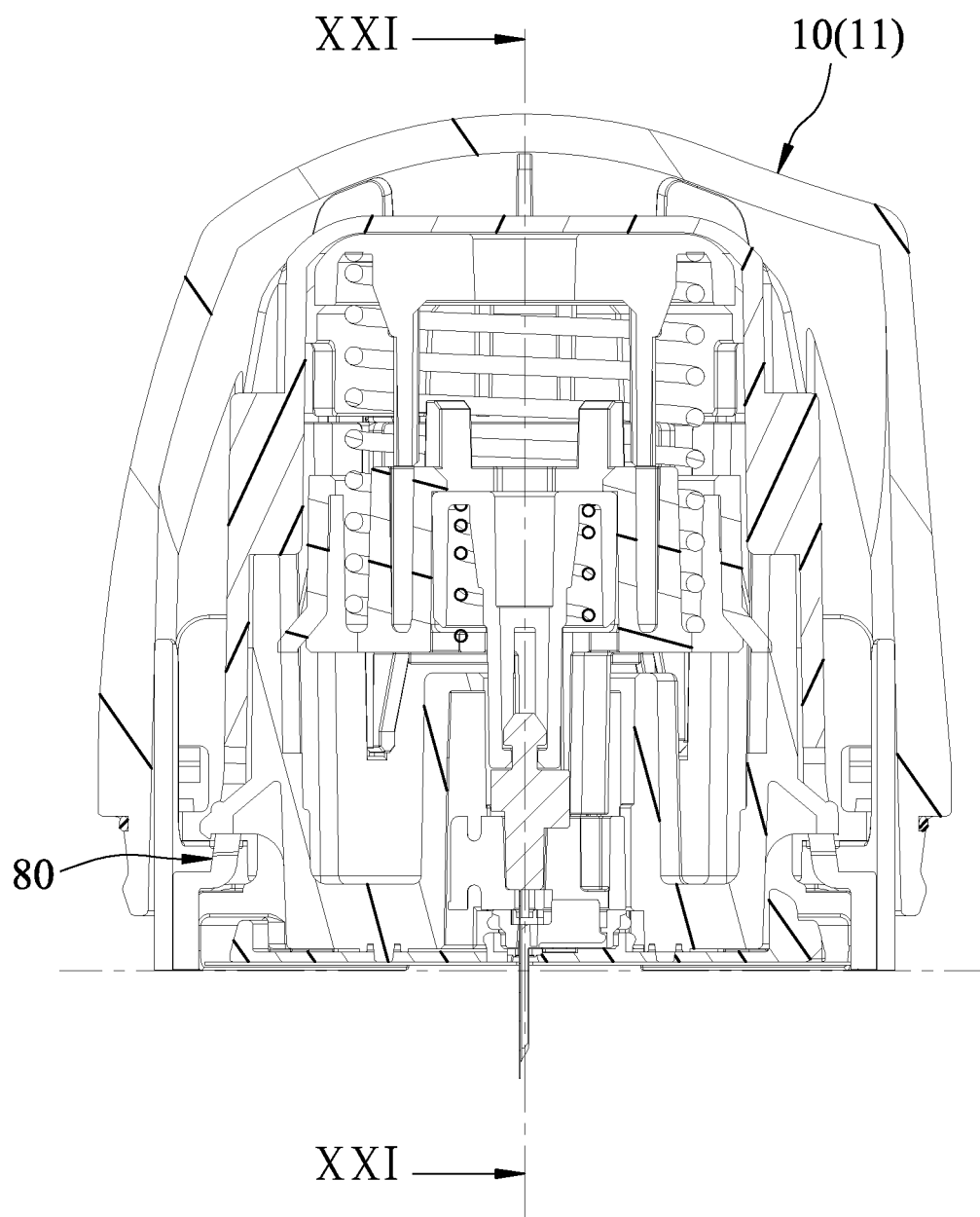
FIG. 20 is another sectional view of the modification, illustrating an instance during the implanting.
Figure 21:
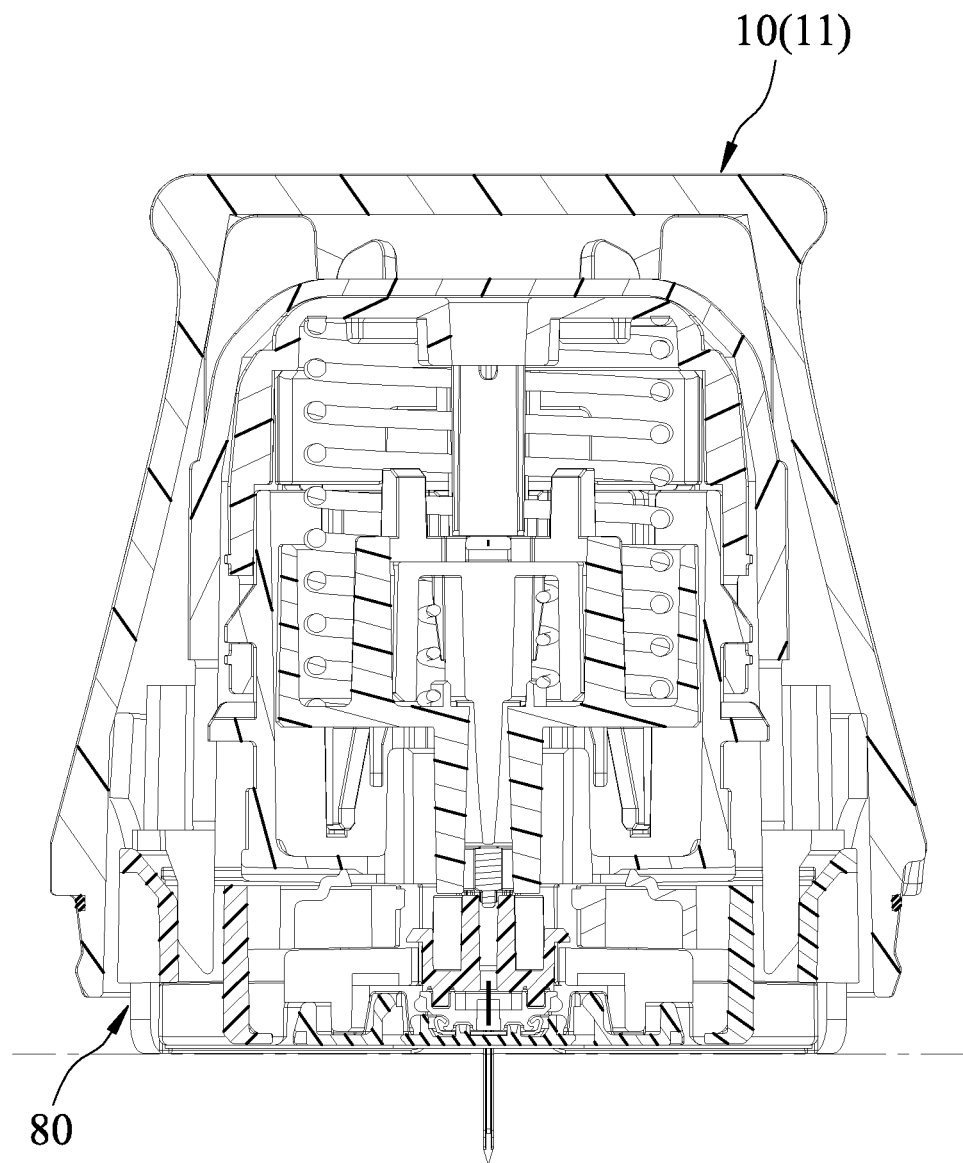
FIG. 21 is a sectional view taken along line XXI-XXI in FIG. 20.
Figure 27:
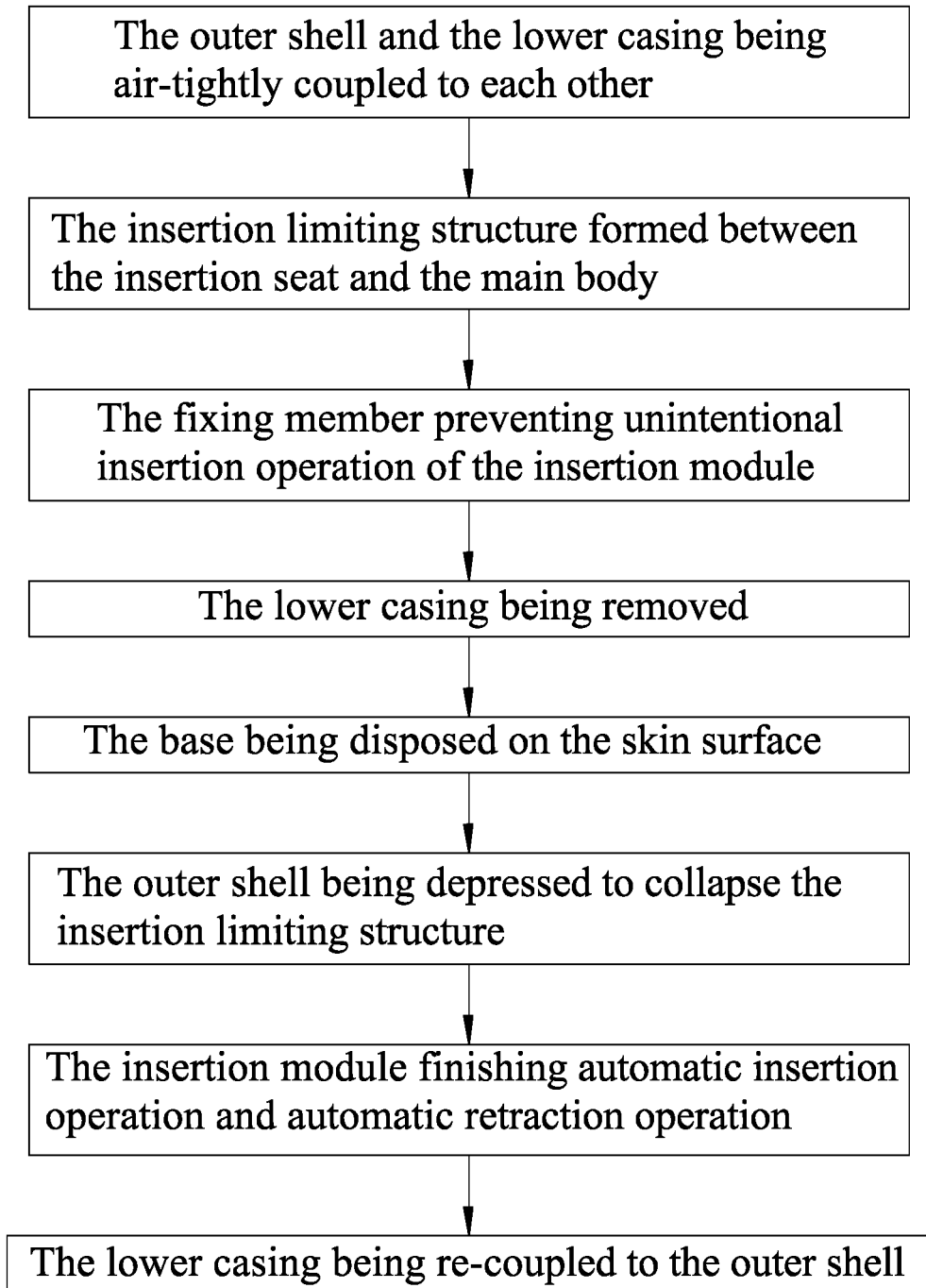
FIG. 27 is a flow chart of an insertion operation of the insertion device according to the disclosure.

Referring to FIGS. 15 and 16, the separated lower casing 20 can be re-coupled to the upper casing 10. The lower casing 20 can seal a bottom portion of the outer shell 11 by the engagement between the annular protruding portion 115 of the upper casing 10 and the annular groove 224 of the lower casing 20. When the lower casing 20 is re-coupled to the outer shell 11 of the upper casing 10, the engagement between the lower positioning portion 227 of the lower casing 20 and the upper positioning portion 116 of the upper casing 10 ensures that the lower casing 20 and the upper casing 10 are properly positioned to each other. In addition, the inner space of the insertion device can serve as a waste storing space. A used base 50 can be removed from the host and be placed in the inner space of the insertion device, such that the used insertion device can be disposed in compliance with standard of discard of medical waste. The whole insertion operation of the insertion device according to the disclosure is shown in FIG. 27.

FIG. 28 shows that after the sensor 72 is implanted under the skin surface P of the living body, the sensor assembly 70 and the base 50 that are simultaneously disposed on the skin surface P of the living body, a transmitter 90 is installed on the base 50 in the form of an upper cover to process the physiological signals measured by the sensor 72 and allows the signals to be transmitted to the outside. In order to reduce the number of components to be implanted during the implantation process and also reduce the loading of the container, the inserter device of the present invention does not include a transmitter. The separately arranged the transmitter 90 and the sensor assembly 70 are to ensure the electronic parts are not damaged by the sterilization process, so the production yield of the device can be improved.

Figure 31:
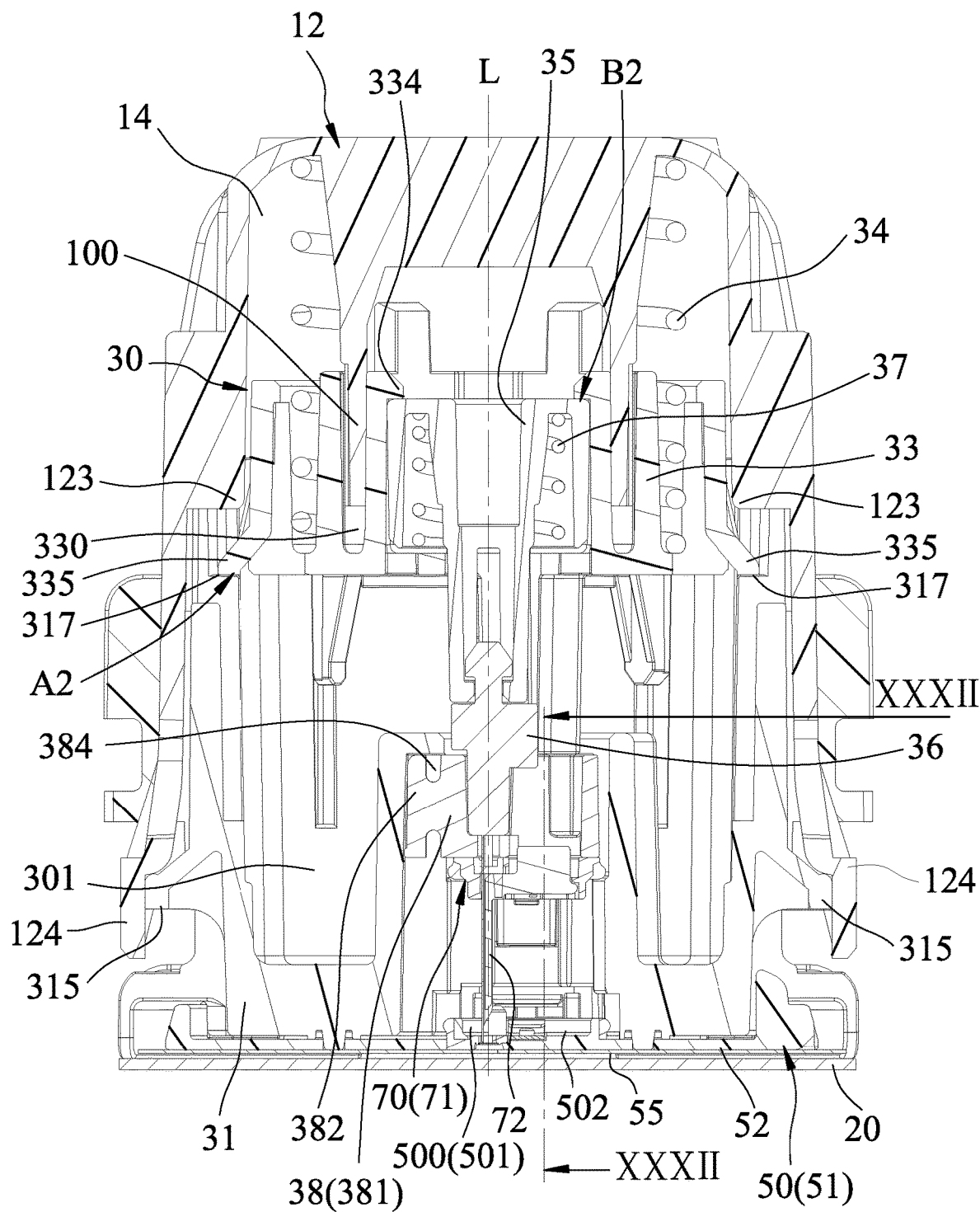
FIG. 31 is a sectional view illustrating a third embodiment of the insertion device according to the disclosure.
Figure 32:
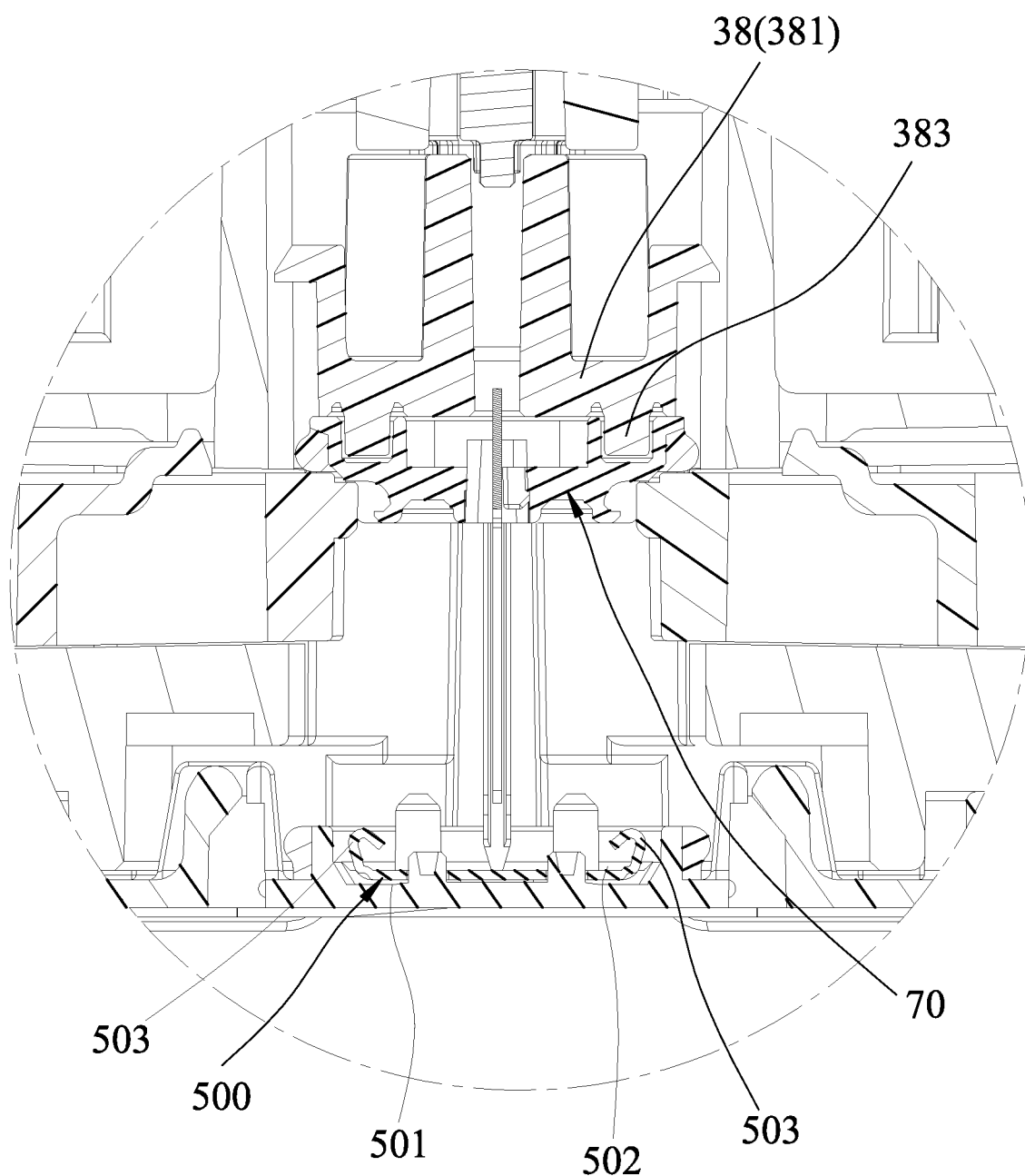
FIG. 32 is an enlarged sectional view of the third embodiment.

Referring to FIGS. 31 and 32, a third embodiment of the insertion device (similar to the automatic needle insertion and automatic needle extraction of the first embodiment, but in this embodiment does not include the outer shell 11) can optionally have a bottom cover 20, or uses a sealed package to seal the insertion device. The insertion device includes a cover body 12 and an insertion module 30.

The cover body 12 has an accommodating space 14, and a pair of casing engaging structures 124.

The insertion module 30 is disposed in the accommodating space 14, and includes a main body 31, an insertion seat 33, a first elastic member 34, a retraction seat 35, a second elastic member 37, a base 50 and a sensor assembly 70.

The main body 31 is associated with the cover body 12, and cooperates with the cover body 12 to define a displacement space 301 therebetween. The main body 31 has a pair of body engaging structures 315 that are able to respectively engage the casing engaging structure 124 of the cover body 12.

The insertion seat 33 is removably positioned in the cover body 12, and is able to move in the displacement space 301 between the main body 31 and the cover body 12 along an axial line (L).

The cover body 12 has a pair of urging portions 123 on an inner surrounding surface thereof. The main body 31 has a pair of stopping portions 317. The insertion seat 33 has a pair of buckle portions 335 that respectively and separably abut against the stopping portions 317 of the main body 31 so as to position the insertion seat 33 relative to the main body 31, and that are able to be respectively pushed by the urging portions 123 of the cover body 12 to be respectively separated from the stopping portions 317 of the main body 31. The buckle portions 335 of the insertion seat 33 respectively and separably abut the stopping portions 317 of the main body 31 so as to form an insertion limiting structure (A2) between the insertion seat 33 and the main body 31.

The insertion seat 33 further has at least one limiting groove 330. The cover body 12 further has at least one limiting member 100 that removably engages with the limiting groove 330 of the insertion seat 33. The insertion seat 33 further has at least one retraction positioning portion 334 that separably abuts against the limiting member 100 of the cover body 12.

The first elastic member 34 has two opposite ends respectively abutting against the insertion seat 33 and the cover body 12. In this embodiment, the first elastic member 34 may be configured as a pre-compressed spring.

The retraction seat 35 is mounted with an insertion needle 36, and is removably positioned relative to the insertion seat 33. The retraction positioning portion 334 of the insertion seat 33 is removably limited by the limiting member 100 of the cover body 12, so as to form a retraction limiting structure (B2) that positions the retraction seat 35 relative to the insertion seat 33.

The second elastic member 37 has two opposite ends respectively abutting against the insertion seat 33 and the retraction seat 35. In this embodiment, the second elastic member 37 may be configured as a pre-compressed spring.

The base 50 is separably positioned relative to the main body 31, and includes a base seat 51, and an adhesive pad 52 that is fixedly connected to the base seat 51.

The sensor assembly 70 is to be separably mounted to the base 50, and includes a sensing seat 71, and a sensor 72 that is mounted to the sensing seat 71 and that is separably coupled to the insertion needle 36. The base 50 further has a mounting portion 500 for the sensor assembly 70 to be separably mounted thereto, and the mounting methods are similar as those described in the previous embodiment. The insertion module 30 further includes an auxiliary insertion seat 38 that is separably mounted to the insertion needle 36. The sensor assembly 70 is separably mounted to the auxiliary insertion seat 38. The auxiliary insertion seat 38 slidably engages with the main body assembly 300 to guide the insertion needle 36 to steadily insert the sensor 72 into the host without runout or inclination so as to alleviate pain of the host.

Figure 33:
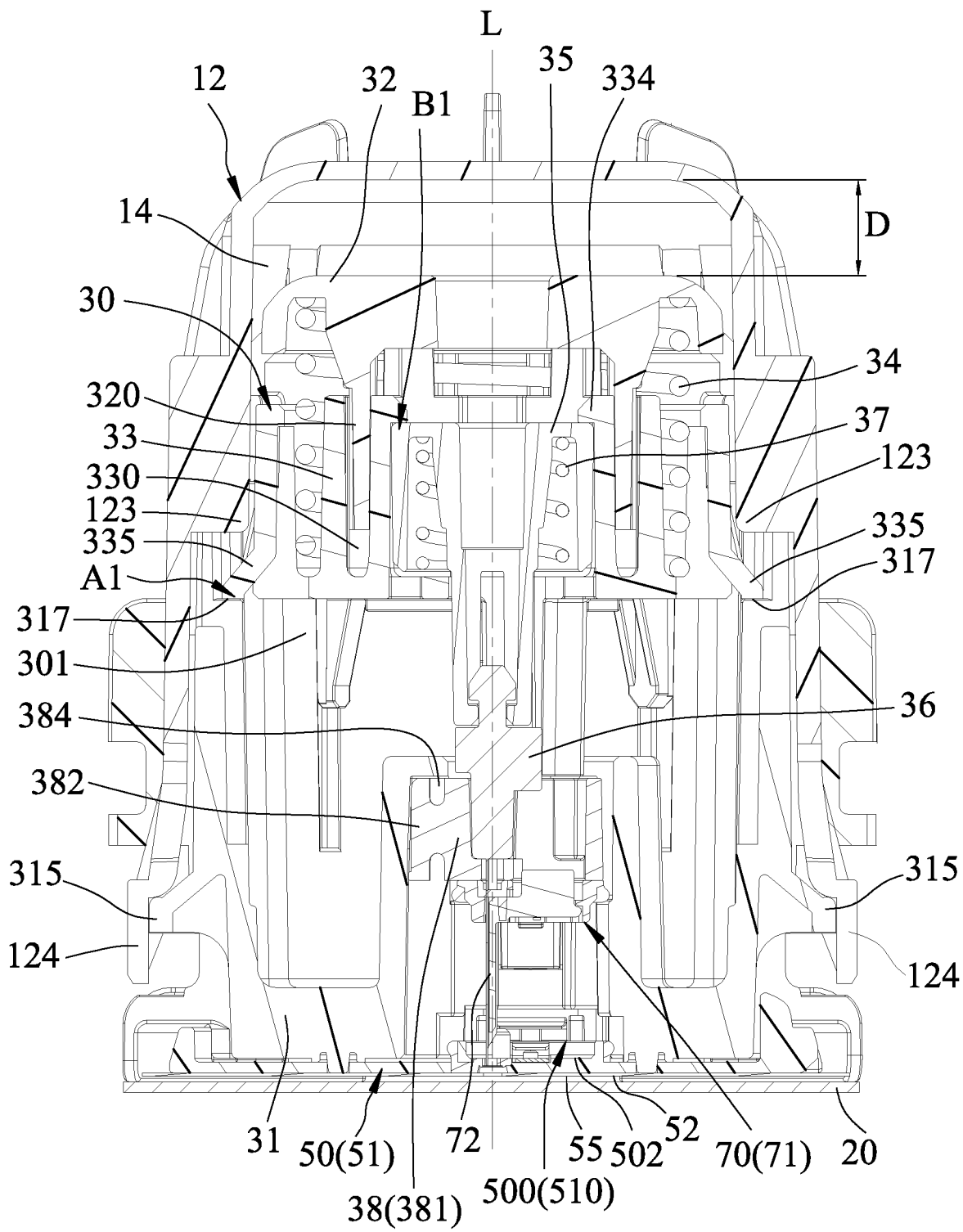
FIG. 33 is a sectional view illustrating a fourth embodiment of the insertion device according to the disclosure.

Referring to FIG. 33, a fourth embodiment of the insertion device according to the disclosure (similar to the third embodiment but the insertion module includes independent main cover) includes a cover body 12 and an insertion module 30.

The cover body 12 has an accommodating space 14, and a pair of casing engaging structures 124.

The insertion module 30 is disposed in the accommodating space 14, and includes a main body 31, a main cover 32, an insertion seat 33, a first elastic member 34, a retraction seat 35, a second elastic member 37, a base 50 and a sensor assembly 70.

The main body 31 is connected to the main cover 32, and cooperates with the main cover 32 to define a displacement space 301 therebetween. The main body 31 has a pair of body engaging structures 315 that are able to respectively engage the casing engaging structure 124 of the cover body 12. A top portion of the cover body 12 and a top portion of the main cover 32 is spaced apart from each other by a distance (D).

The insertion seat 33 is removably positioned in the main cover 32, and is able to move in the displacement space 301 between the main body 31 and the main cover 32 along an axial line (L).

The cover body 12 has a pair of urging portions 123 on an inner surrounding surface thereof. The main body 31 has a pair of stopping portions 317. The insertion seat 33 has a pair of buckle portions 335 that respectively and separably abut against the stopping portions 317 of the main body 31 so as to position the insertion seat 33 relative to the main body 31, and that are able to be respectively pushed by the urging portions 123 of the cover body 12 to be respectively separated from the stopping portions 317 of the main body 31. The buckle portions 335 of the insertion seat 33 respectively and separably abut the stopping portions 317 of the main body 31 so as to form an insertion limiting structure (A1) between the insertion seat 33 and the main body 31.

The insertion seat 33 further has at least one limiting groove 330. The main cover 32 further has at least one limiting member 320 that removably engages with the limiting groove 330 of the insertion seat 33. The insertion seat 33 further has at least one retraction positioning portion 334 that separably abuts against the limiting member 320 of the main cover 32.

The first elastic member 34 has two opposite ends respectively abutting against the insertion seat 33 and the main cover 32. In this embodiment, the first elastic member 34 may be configured as a pre-compressed spring.

The retraction seat 35 is mounted with an insertion needle 36, and is removably positioned relative to the insertion seat 33. The retraction positioning portion 334 of the insertion seat 33 is removably limited by the limiting member 320 of the main cover 32, so as to form a retraction limiting structure (B1) that positions the retraction seat 35 relative to the insertion seat 33.

The second elastic member 37 has two opposite ends respectively abutting against the insertion seat 33 and the retraction seat 35. In this embodiment, the second elastic member 37 may be configured as a pre-compressed spring.

The base 50 is separably positioned relative to the main body 31, and includes a base seat 51, and an adhesive pad 52 that is fixedly connected to the base seat 51.

The sensor assembly 70 is to be separably mounted to the base 50, and includes a sensing seat 71, and a sensor 72 that is mounted to the sensing seat 71 and that is separably coupled to the insertion needle 36. The base 50 further has a mounting portion 500 for the sensor assembly 70 to be separably mounted thereto, and the mounting methods are similar as those described in the previous embodiment.

The insertion module 30 further includes an auxiliary insertion seat 38 that is separably mounted to the insertion needle 36. The sensor assembly 70 is separably mounted to the auxiliary insertion seat 38. The auxiliary insertion seat 38 slidably engages with the main body assembly 300 to guide the insertion needle 36 to steadily insert the sensor 72 into the host without runout or inclination so as to alleviate pain of the host.

The insertion device according to the disclosure (the first to fourth embodiments and the modifications thereof) is operated in such a manner that the upper casing 10 or the cover body 12 is depressed so as to collapse the insertion limiting structure (A, A1, A2), and the first elastic member 34 therefore releases the restoring force to move the insertion seat 33 downwardly to perform the automatic-insertion operation. In other words, in this disclosure, the insertion needle 36 is driven to be inserted into the host by the first elastic member 34 rather than by manual depression of a user. Therefore, the insertion operation and the retraction operation can be smoothly performed by any user even if the user is not an adept operator.

The insertion operation performed by the third and fourth embodiments, according to the disclosure are operated via a single-action operation. The insertion operation of the sensor 72 into the host is illustrated as follows:

Referring to FIGS. 31 to 33, when the adhesive pad 52 is adhered to a skin surface of the host and the cover body 12 is not depressed, the insertion limiting structure (A1, A2) that is formed between the buckle portions 335 of the insertion seat 33 and the stopping portions 317 of the main body 31 maintains the insertion seat 33 at a pre-insertion position. When the cover body 12 is depressed toward the skin surface, the buckle portions 335 of the insertion seat 33 are respectively pushed by the urging portions 123 of the cover body 12 to be deformed inwardly and to be respectively separated from the stopping portions 317 of the main body 31, so that the insertion limiting structure (A1, A2) is collapsed. At the same time, the body engaging structures 315 of the main body 31 respectively engage the casing engaging structure 124 of the cover body 12, so that the cover body 12 is positioned relative to the main body 31.

After the insertion limiting structure (A1, A2) is collapsed, the restoring force of the first elastic member 34 is permitted to be released, and moves the insertion seat 33 to an insertion position to implement automatic-insertion, such that the sensor assembly 70 is moved by the insertion seat 33 to a post-insertion position, that the sensor 72 is inserted underneath the skin surface, and that the sensing seat 71 is positioned onto the mounting portion 500 of the base 50. After the sensor 72 is inserted underneath the skin surface, the limiting member 320 of the main cover 32 or the limiting member 100 of the cover body 12 is separated from the limiting groove 330 and the retraction positioning portion 334 of the insertion seat 33, so that the retraction positioning portion 334 is permitted to be deformed outwardly to collapse the retraction limiting structure (B1, B2). As such, the restoring force of the second elastic member 37 is permitted to be released, and drives the retraction seat 35 to move past the retraction positioning portion 334 of the insertion seat 33 away from the skin surface, such that the insertion needle 36 is separated from the auxiliary insertion seat 38 and is retracted into the insertion seat 33 to hide a needle 362 thereof and to implement automatic-retraction. At this time, the coupling portions 383 of the auxiliary insertion seat 38 is maintained to be fitted into the coupling portion 711 of the sensing seat 71 so that the auxiliary insertion seat 38 is connected to the sensing seat 71 of the sensor assembly 70.

Afterward, the cover body 12 and the insertion module 30 are separated from the base 50 and the skin surface of the host, so as to finish the insertion operation of the third and fourth embodiments of the insertion device including the automatic-insertion and automatic-retraction operations.

Accordingly, the third and fourth embodiments of the insertion device may further include a lower casing (not shown) that is air-tightly and separably coupled to the cover body 12 so as to form an airtight space within the insertion device. A desiccant may be provided in the inner space of the insertion device so as to prevent the sensor 72 of the sensor assembly 70 from being moistened.

In the third or fourth embodiments, a time needed for performing the automatic-insertion operation and the automatic-retraction operation (i.e., the duration for which the insertion needle 36 is inserted into the host) is no more than 100 milliseconds, no more than 50 milliseconds, no more than 8 milliseconds, no more than 6 milliseconds, no more than 4 milliseconds or no more than 2 milliseconds;

In the fourth embodiment, by virtue of the main cover 32 that cooperates with the insertion seat 33 to compress the first elastic member 34 therebetween, the restoring force of the first elastic member 34 would not act on the cover body 12 when a user depresses the cover body 12, rendering the operation of the insertion device smooth. The insertion module further includes an insertion seat 33 and a retraction seat 35. The insertion limiting structure (A1, A2) is formed between the insertion seat 33 and the main body 31. The retraction limiting structure (B1, B2) is formed among the insertion seat 33, the retraction seat 35 and the main cover 31 or among the insertion seat 33, the retraction seat 35 and the cover body 12.

The retraction seat 35 includes an insertion needle 36. The insertion seat 33 includes a pushing portion (with reference to the reference numeral 337 in FIG. 3). After the automatic-insertion operation performed by the insertion module 30, the insertion needle 36 is inserted through the base 50 to insert a sensor 72 underneath a skin surface of a host, and the pushing portion of the insertion seat 33 tightly abuts against the sensor assembly 70 (via an auxiliary insertion seat 38) so as to prevent the sensor assembly 70 from being separated from a mounting portion 500 of the base 50.

The advantages of the insertion device according to the disclosure are as follows:

1. The insertion device employs the pre-compressed first and second elastic members 34, 37 to perform the automatic-insertion and automatic-retraction operations, so that insertion device is operated via a single-action operation (i.e., by depressing the upper casing 10, outer shell 11 or the cover body 12) to finish the automatic-insertion and automatic-retraction operations. The insertion needle 36 is not driven to be inserted into the host by manual depression of a user. Therefore, the insertion operation and the retraction operation can be smoothly performed by any user even if the user is not an adept operator.

2. The lower casing 20 cooperates with the upper casing 10 or the cover body 12 to form the airtight space that is provided with the desiccant 60 therein, so that the sensor 72 of the sensor assembly 70 is prevented from being moistened to ensure the accuracy of the sensor assembly 70. In addition, a desiccation indicator 61 (see FIG. 4) may be provided on inner or outer side of the outer shell 11 of the upper casing 10. Preferably, the desiccation indicator 61 may be an aridity indication material. The outer shell 11 may have a transparent or translucent portion through which the desiccation indicator 61 is visible, so a user can perceive whether or not the sensor assembly 70 is moistened. The manner in which the desiccant 60 is disposed is not limited to the disclosed embodiments, and the upper casing 10 and the lower casing 20 are not limited to be interconnected in a hard-interference manner.

3. Before the lower casing 20 is separated (or opened) from the upper casing 10 or from the cover body 12, the abutment portion 228 of the lower casing 20 limits movement of the casing engaging structure 124 of the cover body 12 or the upper casing 10, such that the upper casing 10 or the cover body 12 cannot move downwardly so as to prevent unintentional insertion operation of the insertion device due to unintentionally applying force to the insertion device.
4. After the automatic-retraction operation, the insertion needle 36 is separated from the auxiliary insertion seat 38 and is retracted into the insertion seat 33 to hide a needle 362.
5. By virtue of the main cover 32 that cooperates with the insertion seat 33 to compress the first elastic member 34 therebetween, the restoring force of the first elastic member 34 would not act on the upper casing 10 or the cover body 12 when a user depresses the upper casing 10 or the cover body 12, rendering the operation of the insertion device smooth.
6. The auxiliary insertion seat 38 slidably engages with the main body assembly 300 to guide the insert direction of the insertion needle 36 to steadily insert the sensor 72 into the host without runout or inclination so as to alleviate pain of the host.
7. The base 50 has a mounting portion 500 for the sensor assembly 70 to be separably mounted thereto. The mounting portion 500 may include a recess 501 that permits the sensor assembly 70 to be press-fitted thereinto, and/or an adhesive layer 502 (e.g., double-sided tape) that is disposed in the recess 501 for the sensor assembly 70 to be adhered thereto, or at least one resilient hook 503 that is for engaging with the sensor assembly 70.
8. After the upper casing 10 (or housing 11) or the cover body 12 is depressed, a time needed for performing the automatic-insertion operation and the automatic-retraction operation is no more than 100 milliseconds, no more than 50 milliseconds, no more than 8 milliseconds, no more than 6 milliseconds, no more than 4 milliseconds or no more than 2 milliseconds.
9. In assembling the insertion device, the first elastic member 34, the retraction seat 35, the second elastic member 37 and the insertion seat 33 are firstly disposed between the main cover 32 and the main body 31, and the auxiliary insertion seat 38 and the sensor assembly 70 are mounted to the insertion needle 36 before the insertion needle 36 is mounted to the retraction seat 35. Whereby the sensor assembly 70 and the insertion module 30 forming a clutch design, which can not only greatly improve the assembly yield, but also effectively reduce the cost of the sensor assembly.
10. The sensor assembly 70 has been mounted to the insertion module 30 via the auxiliary insertion seat 38 (see FIG. 29), so the sensor assembly 70 does not require additional manual operation of grasping the sensor assembly 70 onto the base 50 by the implanting module 30.
11. An inner side of a bottom portion of the upper casing 10 may be provided with a cushion wall 80 (see FIGS. 17 to 21) that is substantially ring-shaped. Before the insertion device is operated, the base 50 is higher than a bottom edge of the cushion wall 80. When the bottom edge of the cushion wall 80 abuts against the skin surface of the host, the base 50 is spaced apart from the skin surface, so a user can move the insertion device along the skin surface to a desired position, an depress the upper casing 10. The cushion wall 80 retracts into the upper casing 10 upon the depression, such that the base 50 can be mounted onto the skin surface. By virtue of the cushion wall 80, the insertion device can be moved along the skin surface to a desired position with the cushion wall 80 abutting against the skin surface, rendering the insertion operation stable.
12. When the lower casing 20 is re-coupled to the outer shell 11 of the upper casing 10, the engagement between the lower positioning portion 227 of the lower casing 20 and the upper positioning portion 116 of the upper casing 10 ensures that the lower casing 20 and the upper casing 10 are properly positioned to each other.

In addition to the embodiments described above, this disclosure further discloses a plurality of embodiments as defined by the claims, with each embodiment comprising the claim elements of the respective claim and the claim elements of any claim upon which the respective claim depends.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:
1. An insertion device comprising:
a cover body having a retaining space; and
an insertion module disposed in said retaining space, and including
a main body,
a main cover that is connected to said main body and that cooperates with said main body to define a displacement space therebetween,
an insertion seat that is removably positioned in said main cover and that is able to move in said displacement space between said main body and said main cover,
a pre-compressed first elastic member that has two opposite ends that respectively abut against said insertion seat and said main cover,
a retraction seat that is removably positioned relative to said insertion seat, a pre-compressed second elastic member that has two opposite ends that respectively abut against said insertion seat and said retraction seat,
a base that is separably positioned relative to said main body, and
a sensing assembly that is to be separably mounted to said base;
wherein the insertion device is configured such that depression of said cover body to move toward a skin surface relative to said main body causes the insertion seat to be driven by a restoring force of said pre-compressed first elastic member to perform an automatic-insertion operation of a sensor under said skin surface and causes a collapse of a first limiting structure between said insertion seat and said main body, said sensing assembly and said base being separated from each other before the automatic-insertion operation, and being coupled to each other after the automatic-insertion operation;
wherein the insertion device is further configured such that, after the automatic-insertion operation is done and after a force that implements said depression of said cover body to move toward the skin surface is removed, said cover body is positioned relative to said main body without rebounding away from the skin surface, and a second limiting structure between said insertion seat and said retraction seat collapses upon the collapse of said first limiting structure between said insertion seat and said main body, so that said retraction seat is driven by a restoring force of said pre-compressed second elastic member to perform an automatic-retraction operation; and
wherein the insertion device is further configured such that the restoring force of said pre-compressed first elastic member is configured not to act on said cover body during the depression of said cover body.

2. The insertion device as claimed in claim 1, wherein said retraction seat is mounted with an insertion needle.

3. The insertion device as claimed in claim 1, wherein said insertion seat has at least one limiting groove, said main cover having at least one limiting member that removably engages with said at least one limiting groove of said insertion seat, said insertion seat further having at least one positioning portion that positions said retraction seat relative to said insertion seat, said at least one limiting groove cooperating with said at least one limiting member and said at least one positioning portion to form a retraction limiting structure among said insertion seat, said retraction seat and said main cover that serves as said second limiting structure.

4. The insertion device as claimed in claim 1, wherein said cover body has at least one urging portion on an inner surrounding surface thereof, said main body having at least one stopping portion, said insertion seat having at least one buckle portion that separably abuts against said at least one stopping portions of said main body so as to position said insertion seat relative to said main body, said buckle portion being able to be pushed by said at least one urging portion of said cover body to be separated from said at least one stopping portion of said main body, said at least one buckle portion of said insertion seat cooperating with said at least one stopping portion of said main body to form an insertion limiting structure between said insertion seat and said main body that serves as said first limiting structure.

5. The insertion device as claimed in claim 1, wherein each of said pre-compressed first elastic member and said pre-compressed second elastic member is configured as a pre-compressed spring.

6. The insertion device as claimed in claim 1, further comprising a lower casing that is air-tightly and separably coupled to said cover body so as to formed an airtight space within said insertion device, said airtight space being provided with a desiccant therein.

7. The insertion device as claimed in claim 1, wherein said cover body has at least one casing engaging structure, said main body having at least one body engaging structure that is able to engage said casing engaging structure of said cover body said body engaging structure of said main body being operated to engage said casing engaging structure of said cover body when said cover body is depressed toward the skin surface of a host to perform the automatic-insertion operation, so that said cover body is positioned relative to said main body without rebounding after the force that depresses said cover body toward the skin surface is removed.

8. The insertion device as claimed in claim 1, wherein said base has a mounting portion for a sensor assembly to be separably mounted thereto, said mounting portion of said base including a recess that permits said sensor assembly to be press-fitted thereinto and that is provided with an adhesive layer therein for said sensor assembly to be adhered thereto, or at least one resilient hook that is for engaging with said sensor assembly.

9. The insertion device as claimed in claim 1, wherein said insertion module further includes an auxiliary insertion seat that is separably mounted to an insertion needle, and wherein a sensor assembly is separably mounted to said auxiliary insertion seat.

10. The insertion device as claimed in claim 1, wherein a time needed for performing the automatic-insertion operation and the automatic-retraction operation is no more than 100 milliseconds, no more than 8 milliseconds, no more than 4 milliseconds or no more than 2 milliseconds.

11. An insertion method of a sensor, comprising:
providing an insertion device including a displacement space that is cooperatively defined by a main cover and a main body;
providing an insertion module disposed in the displacement space, the insertion module being movable in the displacement space by pre-compressed first and second elastic members therein so as to perform an automatic-insertion operation and an automatic-retraction operation;
providing an insertion limiting structure disposed between the insertion module and the main body for removably positioning the insertion module at a pre-insertion position;
providing a retraction limiting structure disposed between the insertion module and the main cover, a portion of the insertion module being able to move from a post-insertion position to the pre-insertion position when the retraction limiting structure is collapsed; and
depressing the insertion device downwardly to move a cover body relative to the main body toward a skin surface such that the depressing causes the insertion limiting structure to be collapsed and causes the insertion module to be biased by a restoring force of the pre-compressed first elastic member to move downwardly to perform the automatic-insertion operation of the sensor under the skin surface, the retraction limiting structure being collapsed immediately after the insertion module finishing the automatic-insertion operation, such that the insertion module is biased by a restoring force of the pre-compressed second elastic member to move upwardly to perform the automatic-retraction operation, the insertion module positioning a sensor assembly thereof onto a base during the automatic-insertion operation, a time needed for performing the automatic-insertion operation and the automatic-retraction operation being no more than 100 milliseconds, no more than 8 milliseconds, no more than 4 milliseconds or no more than 2 milliseconds, the sensing assembly and the base being separated from each other before the automatic-insertion operation, and being coupled to each other after the automatic-insertion operation, the cover body being positioned relative to the main body without rebounding away from the skin surface after a force that implements said depressing of the insertion device downwardly to move the cover body relative to the main body toward the skin surface is removed.

12. The insertion method as claimed in claim 11, wherein the insertion module includes an insertion seat and a retraction seat, the insertion limiting structure being formed between the insertion seat and the main body, the retraction limiting structure being formed among the insertion seat, the retraction seat and the cover body, the retraction seat being mounted with an insertion needle, the insertion seat having a pushing portion.

13. The insertion method as claimed in claim 12, wherein the base has a mounting portion that corresponds in position to the sensor assembly, the mounting portion of the base including a recess that permits the sensor assembly to be press-fitted thereinto and that is provided with an adhesive layer therein for the sensor assembly to be adhered thereto, or at least one resilient hook that is for engaging with the sensor assembly.

14. The insertion method as claimed in claim 13, wherein, after the insertion operation performed by the insertion device, the insertion needle is inserted through the base to insert the sensor under the skin surface, wherein the skin surface is a skin surface of a host, and the pushing portion of the insertion seat tightly abuts against the sensor assembly so as to prevent the sensor assembly from being separated from a mounting portion of the base.

15. The insertion method as claimed in claim 13, wherein the pre-compressed first elastic member is configured as a pre-compressed spring, and has two opposite ends that respectively abut against the insertion seat and the main cover.

16. The insertion method as claimed in claim 13, wherein the pre-compressed second elastic member is configured as a pre-compressed spring, and has two opposite ends that respectively abut against the insertion seat and the retraction seat.

17. The insertion method as claimed in claim 11, wherein the insertion device further comprising a lower casing that is air-tightly and separably coupled to said cover body so as to formed an airtight space within said insertion device, said airtight space being provided with a desiccant therein.

\* \* \* \* \*